United States Patent
Fadem et al.

(10) Patent No.: US 9,662,034 B2
(45) Date of Patent: May 30, 2017

(54) BIOMARKER FUSION SYSTEM AND METHOD

(75) Inventors: Kalford C. Fadem, Louisville, KY (US); Mauktik V. Kulkarni, Louisville, KY (US)

(73) Assignee: Neuronetrix Solutions, LLC, Louisville, KY (US)

( * ) Notice: Subject to any disclaimer, the term of this patent is extended or adjusted under 35 U.S.C. 154(b) by 349 days.

(21) Appl. No.: 13/228,626

(22) Filed: Sep. 9, 2011

(65) Prior Publication Data

US 2012/0066238 A1   Mar. 15, 2012

Related U.S. Application Data

(60) Provisional application No. 61/381,737, filed on Sep. 10, 2010.

(51) Int. Cl.
| G06F 7/00 | (2006.01) |
| G06F 17/30 | (2006.01) |
| A61B 5/0484 | (2006.01) |
| A61B 5/0478 | (2006.01) |
| A61B 5/00 | (2006.01) |

(52) U.S. Cl.
CPC .......... *A61B 5/0484* (2013.01); *A61B 5/0478* (2013.01); *A61B 5/4088* (2013.01); *A61B 5/6814* (2013.01); *A61B 5/04845* (2013.01)

(58) Field of Classification Search
USPC ................................ 707/736, 737, 755, 758
See application file for complete search history.

(56) References Cited

U.S. PATENT DOCUMENTS

| 5,479,934 A | 1/1996 | Imran |
| 2005/0215916 A1 | 9/2005 | Fadem et al. |
| 2006/0135854 A9 * | 6/2006 | McDonough et al. ....... 600/300 |
| 2007/0027636 A1 * | 2/2007 | Rabinowitz .................... 702/20 |
| 2007/0106169 A1 | 5/2007 | Fadem |
| 2007/0191727 A1 | 8/2007 | Fadem |
| 2007/0270678 A1 | 11/2007 | Fadem et al. |

(Continued)

FOREIGN PATENT DOCUMENTS

| JP | 2008/517636 | 5/2008 |
| JP | 2010/517644 | 5/2010 |

(Continued)

OTHER PUBLICATIONS

U.S. Appl. No. 61/381,569, filed Sep. 10, 2010, Fadem.
Japanese Office Action dated Jul. 14, 2015 for Application No. JP 2013-528312.

*Primary Examiner* — M D. I Uddin
(74) *Attorney, Agent, or Firm* — Frost Brown Todd LLC

(57) ABSTRACT

An apparatus comprises an ERP testing system that is configured to administer an ERP test. The apparatus further comprises a computer in communication with the ERP testing system. The computer is operable to access a database of biomarkers. The computer is further operable to define at least one class set relating to biomarkers and at least one feature set relating to biomarkers. The computer is further operable to classify a test subject into at least one of the defined class sets based on information in the feature set relating to biomarkers of the test subject. The biomarker processing may be carried out in association with or completely independent of ERP testing.

19 Claims, 30 Drawing Sheets

(56) References Cited

U.S. PATENT DOCUMENTS

| | | |
|---|---|---|
| 2008/0208072 A1 | 8/2008 | Fadem et al. |
| 2010/0076780 A1* | 3/2010 | Mahesh et al. .................. 705/2 |
| 2010/0114598 A1* | 5/2010 | Oez ................................. 705/2 |
| 2010/0115288 A1* | 5/2010 | Monk et al. .................. 713/189 |
| 2010/0190686 A1* | 7/2010 | Wells et al. ...................... 514/3 |
| 2011/0016432 A1* | 1/2011 | Helfman ...................... 715/843 |

FOREIGN PATENT DOCUMENTS

| | | |
|---|---|---|
| WO | WO 2009/103156 | 8/2009 |
| WO | WO 2011/038103 | 3/2011 |

* cited by examiner

Fig. 30

BIOMARKER FUSION SYSTEM AND METHOD

PRIORITY

This application claims priority to U.S. Provisional Application Ser. No. 61/381,737, filed Sep. 10, 2010, entitled "Biomarker Fusion System and Method," the disclosure of which is incorporated by reference herein.

BACKGROUND

In some settings, it may be desirable to position a headset with electrodes on a test subject's head, such as to test the subject for various conditions, including but not limited to various types of diseases or conditions within the cerebral cortex, Alzheimer's, Parkinson's, dyslexia, autism, and/or schizophrenia, among other conditions. For instance, one or more system components may be used to provide one or more types of stimuli to the test subject (e.g., auditory, visual, and/or tactile stimulus, etc.); and electrodes may be used to detect Evoked Response Potentials (ERP's) associated with such stimuli. By way of example only, active or locally amplified electrodes, as well as related systems and methods, are discussed in the following documents, each of which is incorporated by reference herein: U.S. Pat. No. 5,479,934, entitled "EEG Headpiece with Disposable Electrodes and Apparatus and System and Method for Use Therewith," issued Jan. 2, 1996; U.S. Pub. No. 2005/0215916, entitled "Active, Multiplexed Digital Electrodes for EEG, ECG, and EMG Applications," published Sep. 29, 2005; U.S. Pub. No. 2007/0106169, entitled "Method and System for an Automated E.E.G. System for Auditory Evoked Responses," published May 10, 2007; U.S. Pub. No. 2007/0270678, entitled "Wireless Electrode for Biopotential Measurement," published Nov. 22, 2007; and U.S. Pub. No. 2007/0191727, entitled "Evoked Response Testing System for Neurological Disorders," published Aug. 16, 2007. It should be understood that the teachings herein may be applied to or otherwise combined with any of the systems and methods taught in all of the above-cited documents. Various ways in which the teachings herein may be applied to or otherwise combined with any of the systems and methods taught in all of the above-cited documents will be apparent to those of ordinary skill in the art.

While a variety of systems have been made and used, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 30 depicts an exemplary screenshot view of an exemplary user interface for the biomarker fusion system of FIG. 11, showing a one-touch classification window;

Figure 1:
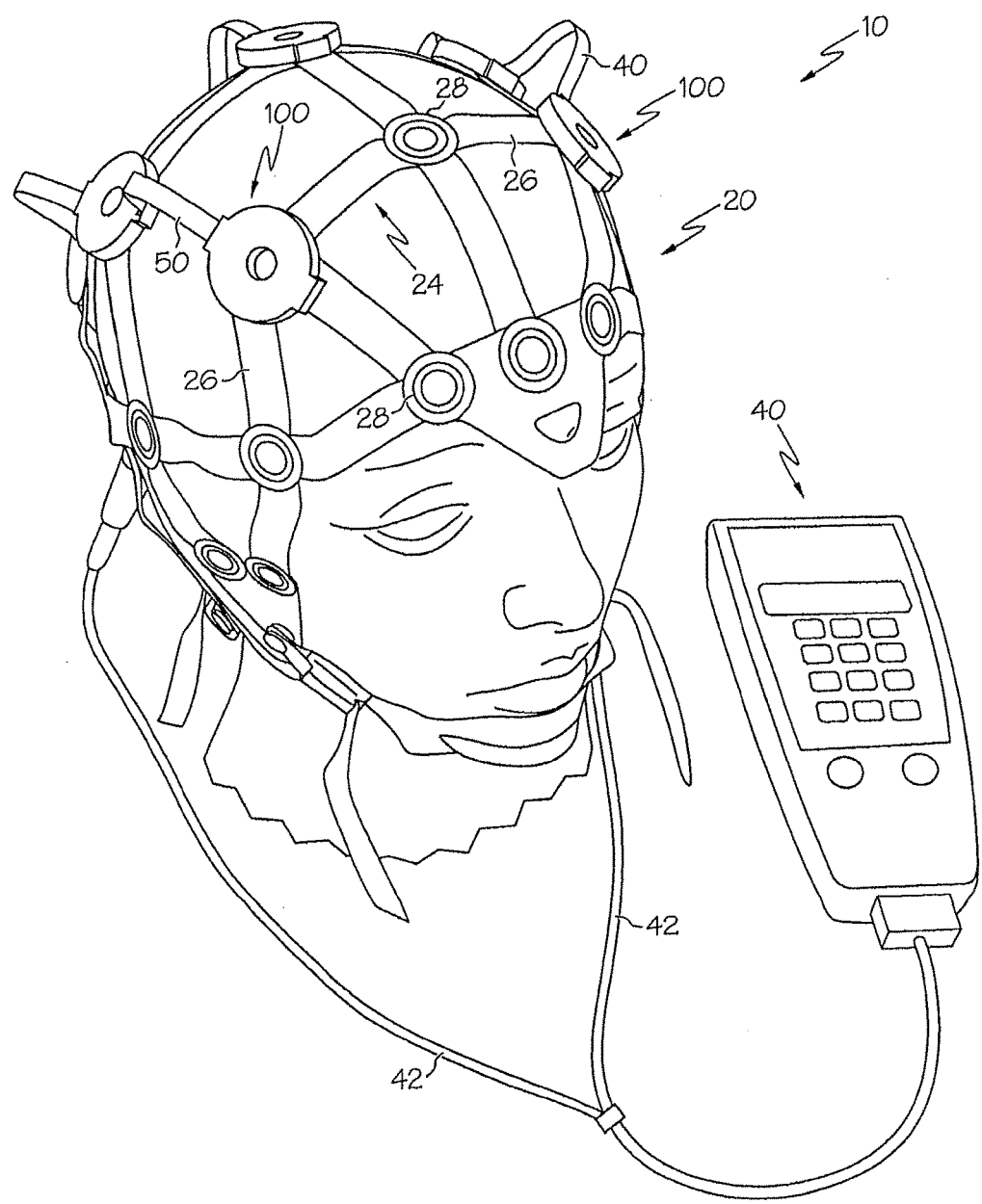
FIG. 1 depicts a perspective view of an exemplary ERP testing system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview of Exemplary ERP Testing System

Examples of components that may be incorporated into an ERP system are shown in FIGS. 1-9 and are described in greater detail below. Of course, an ERP system may have various other components, configurations, and operabilities, including but not limited to any of the various components, configurations, and operabilities described in any of the various documents that are cited and incorporated by reference herein.

A. Exemplary System Overview

Figure 2:
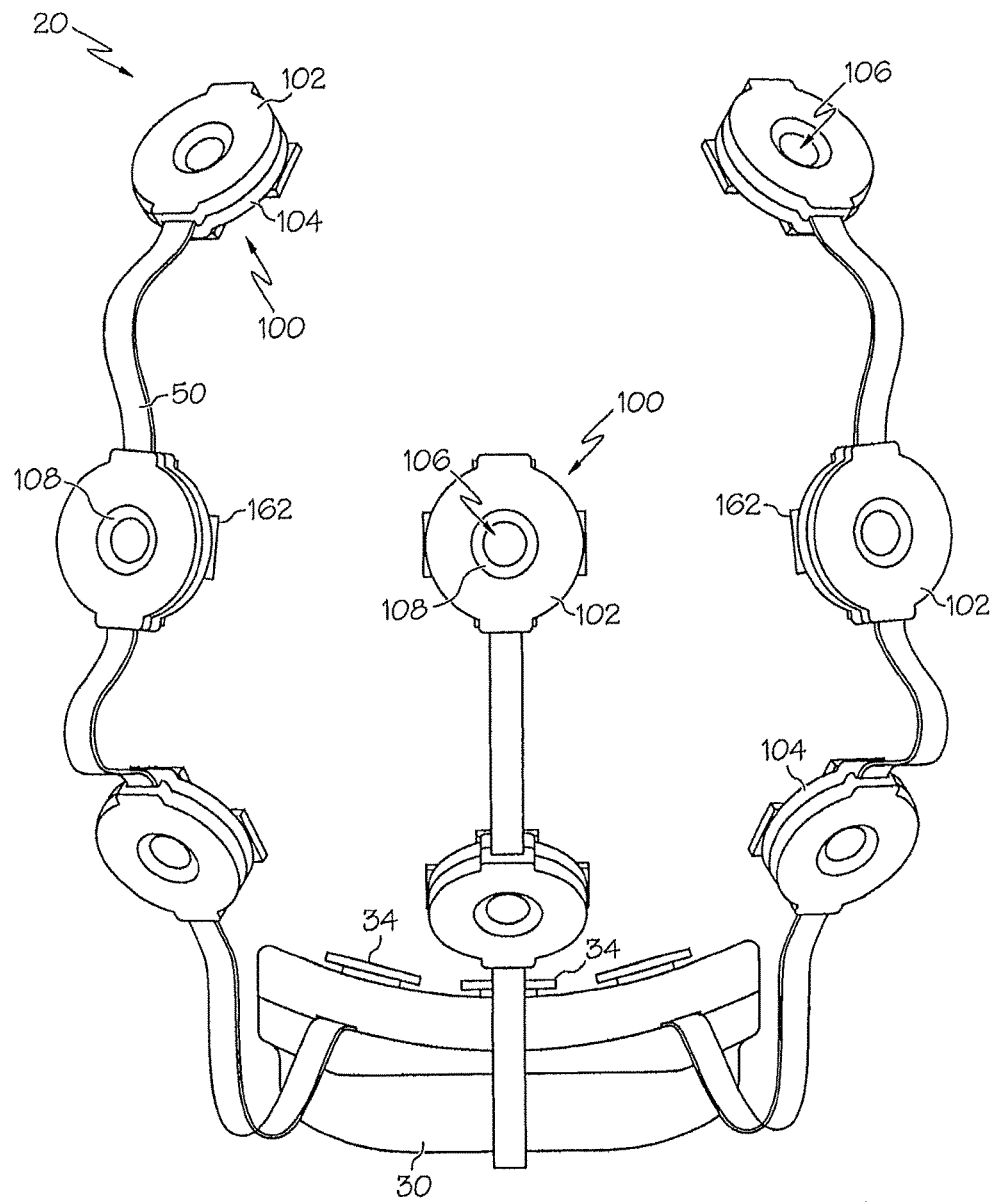
FIG. 2 depicts a top plan view of electrode components of the ERP testing system of FIG. 1.
Figure 3:
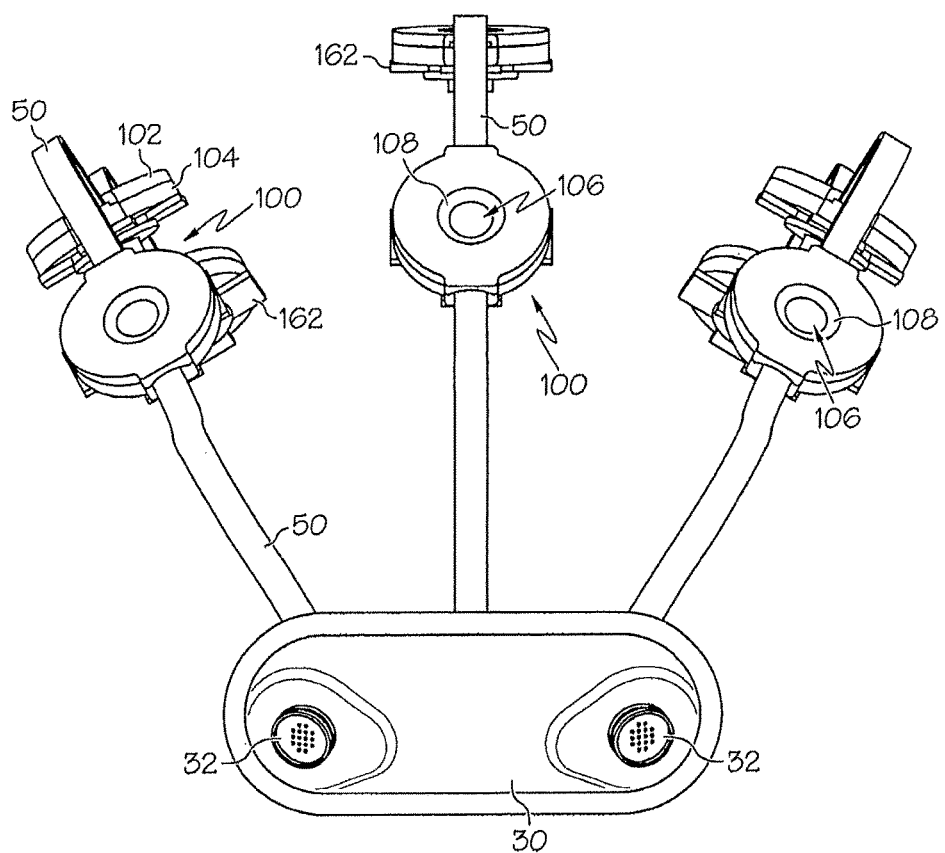
FIG. 3 depicts a rear elevational view of the electrode components of FIG. 2.
Figure 4:
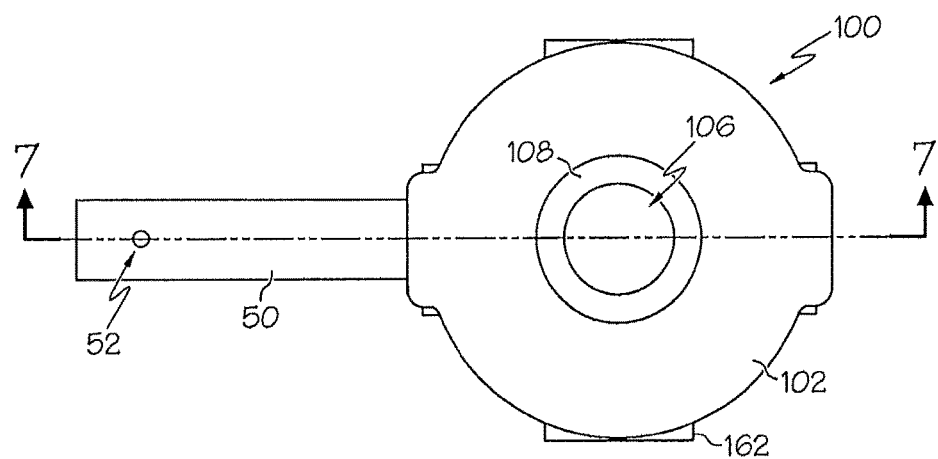
FIG. 4 depicts a top plan view of an electrode module of the electrode components of FIG. 2.

As shown in FIG. 1, an exemplary electrode system (10) includes a headset (20) and a control box (40). Headset (20) comprises a head frame (24) and a plurality of electrode modules (100). While headset (20) of the present example comprises eight electrode modules (100), it should be understood that any other suitable number of electrode modules (100) may be used. It should also be understood that the arrangement of electrode modules (100) shown in FIGS. 1-3 is merely exemplary; and that electrode modules (100) may be positioned in any other suitable arrangement. Electrode modules (100) are removably coupled with head frame (24) as will be described in greater detail below.

B. Exemplary Head Frame

In the present example, head frame (24) is formed of several resilient straps (26), and electrode modules (100) are secured to head frame (24) at junctions of resilient straps (26). The junctions of resilient straps (26) comprise annular snap members (28), which are each open at their center. As will be described in greater detail below, openings (106) of electrode modules (100) are configured to align with the open centers of corresponding snap members (28), to allow inserted sensors (200) to contact the test subject's head. In some versions, resilient straps (26) are formed of elastic, though it should be understood that any other suitable material or combination of materials may be used. While head frame (24) of the present example is configured to substantially encompass a test subject's head, it should also be understood that head frame (24) may have any other suitable configuration. By way of example only, head frame (24) may comprise a EzeNet® reusable head piece by HydroDot, Inc. of Westford, Mass. A EzeNet® reusable head piece may come in various sizes and conform to the international 10/20 system of electrode placement.

As another merely illustrative example, head frame (24) may be configured and/or operable in accordance with the teachings of U.S. Pub. No. 2007/0191727, entitled "Evoked Response Testing System for Neurological Disorders," published Aug. 16, 2007, the disclosure of which is incorporated by reference herein; and/or in accordance with the teachings of any other document cited herein. Indeed, various ways in which the teachings herein may be combined with the teachings of U.S. Pub. No. 2007/0191727 and/or the teachings of any other document cited herein will be apparent to those of ordinary skill in the art. Alternatively, head frame (24) may have any other suitable configuration and/or operability. Other suitable variations of head frame (24) will be apparent to those of ordinary skill in the art in view of the teachings herein.

As shown in FIGS. 1-3, electrode modules (100) are physically and communicatively coupled with each other via flexible connectors (50). Electrode modules (100) are also physically and communicatively coupled with a control box interface module (30) via flexible connectors (50). Flexible connectors (50) of the present example comprise flexible circuits, which comprise traces (not shown) formed in a flexible substrate. Alternatively, conventional wires or other conduits may be used. In the present example, headset (20) is coupled with control box (40) via cables (42). In particular, control box interface module (30) includes ports (32), with which cables (42) may be coupled. Control box interface module (30) also includes circuitry configured to route signals between flexible connectors (50) and cables (42) via ports (32). Control box interface module (30) may thus provide a communicative interface between cables (42) and flexible connectors (50). Various suitable components that may be incorporated into control box interface module (30), as well as various suitable features/functionalities of such components, are described in the documents cited herein. By way of example only, control box interface module (30) may be constructed and operable in accordance with the headset "control module 12" teachings of U.S. Pub. No. 2007/0191727 and/or the teachings of any other document cited herein. Still other suitable components that may be incorporated into control box interface module (30) will be apparent to those of ordinary skill in the art in view of the teachings herein.

In the present example, and as shown in FIG. 2, control box interface module (30) also includes flanged members (34). Flange members (34) are configured to secure control box interface module (30) with head frame (24). For instance, head frame (24) may include openings that are configured to receive flanged members (34). Of course, control box interface module (30) may be secured to head frame (24) in a variety of other ways as will be appreciated by those of ordinary skill in the art, to the extent that control box interface module (30) is secured to head frame (24) at all. Furthermore, control box interface module (30) may simply be omitted in some versions (e.g., cables (42) couple directly to freely hanging flexible connectors (50), etc.).

In some merely exemplary versions, headset (20) comprises a yoke. Such a yoke may comprise a module in headset (20) that contains second stage amplifiers, filters, one or more A/D converters, and/or audio electronics, among other things. As one merely illustrative example, a yoke may be provided by control box interface module (30). The yoke may be operable to provide circuit configuration for gain verification, provide circuit configuration for electrode impedance measurements, execute electrode harness error detection and reporting, and attenuate audio. It will be appreciated that the yoke may have yoke firmware programmed to perform the above listed functions. In some exemplary versions, the yoke firmware may not be upgradeable. In other exemplary versions the yoke firmware will be upgradeable. As a result, in the event that the yoke firmware is upgradeable, the yoke firmware need not necessarily be loaded prior to distribution of the yoke with control box (40). It may be upgraded after distribution. Other suitable ways in which a yoke may be configured and operated will be apparent to those of ordinary skill in the art in view of the teachings herein.

C. Exemplary Control Box

Control box (40) of the present example includes a storage medium (not shown) that is configured to store various testing protocols (e.g., ERP testing protocols, etc.); and a processor (not shown) that is configured to execute such testing via headset (20). In particular, control box (40) provides power and commands or other types of signals to headset (20) via cables (42) in the present example; while headset (20) transmits data or other types of signals back to control box (40) via cables (42). Control box (40) is also operable to store data collected during such testing, including but not limited to data obtained through electrode modules (100). Such power, commands, data, or other types of signals may be provided in accordance with various types of ERP testing protocols as described herein and as described in the documents that are incorporated by reference herein.

Control box (40) is configured to be coupled with a computer system (not shown) via wire and/or wirelessly. For instance, a computer system may transmit testing protocols, commands, or other data to control box (40). Similarly, control box (40) may transmit commands, test results, or other data to a computer system. Control box (40) of the present example is also configured to be handheld. By way of example only, control box (40) may be held in the hand of the test subject who is wearing headset (40), in the hand of a clinician or nurse, or in the hand of any other person. In addition to or in lieu of the foregoing, control box (40) may be configured in accordance with, operable in accordance with, and/or possess any suitable features/functionalities of similar components described in any of the documents cited herein, including but not limited to U.S. Pub. No. 2007/0191727. Various ways in which the teachings herein may be incorporated into or otherwise combined with the teachings of the documents that are cited herein will be readily apparent to those of ordinary skill in the art.

While two cables (42) are shown, it should be understood that just one cable (42) may be used. It should also be understood that some other versions of electrode system (10) may provide communication of power, commands, data, and/or other types of signals to and/or from headset (20) wirelessly, in addition to or in lieu of having cables (22).

D. Exemplary Electrode Module

In the present example, electrode modules (100) of electrode system (10) are substantially identical to each other. The following description will therefore just describe an individual electrode module (100) as an example. It should be understood, however, that a given electrode system (10) may have different types of electrode modules (100). In other words, one or more electrode modules (100) within a given electrode system (10) may have features, components, functionalities, etc., that differ from the features, components, functionalities, etc., of other electrode modules (100) within the same electrode system (10). Such differences among electrode modules (100) may be based on a variety of considerations, including but not limited to the location of electrode module (100) on the test subject's head or other part of the test subject's anatomy. Suitable ways in which electrode modules (100) may differ from each other within a given electrode system (10) will be apparent to those of ordinary skill in the art in view of the teachings herein. Alternatively, as in the present example, all electrode modules (100) within a given electrode system (10) may be substantially identical to each other.

As shown in FIGS. 2-7, electrode module (100) comprises an upper clamshell member (102), a lower clamshell member (104), a circuit board (130), and a conductive ring (150). Clamshell members (102, 104) may be formed of molded plastic and/or using any other suitable material(s) and/or process(es). As shown, upper clamshell member (102), lower clamshell member (104), circuit board (130), and conductive ring (150) all define a central opening (106). In particular, the central openings of upper clamshell member (102), lower clamshell member (104), circuit board (130), and conductive ring (150) are all configured to coaxially align when these components are assembled together to form electrode module (100), such that the assembled electrode module (100) itself defines a central opening (106). This central opening (106) is configured to insertingly receive a sensor (200) as will be described in greater detail below. In addition, these components are configured such that a portion of conductive ring (150) is exposed in the inner diameter of the central opening (106) of the assembled electrode module (100), as will also be described in greater detail below. During assembly of electrode module (100), upper clamshell member (102) may be secured to lower clamshell member (104) using any suitable technique or techniques, including but not limited to ultrasonic welding, snap-fitting, adhesives, fasteners, etc. While opening (106) is at the approximate center of electrode module (100) in the present example, it should be understood that opening (106) may be located off-center or otherwise relative to the remainder of electrode module (100).

Upper clamshell member (102) of the present example presents an annular inclined surface (108) at the perimeter of opening (106). Annular inclined surface (108) is configured to facilitate insertion of sensor (200) into opening (106) as will be described in greater detail below. Of course, as with other components and features described herein, inclined surface (108) is merely optional. Lower clamshell member (104) of the present example comprises a first pair of upwardly extending posts (110) and a second pair of upwardly extending posts (112). Lower clamshell member (104) also includes an annular rim (114) at the perimeter of opening (106) and a trench (116) adjacent to annular rim (114). Each of these features of lower clamshell member (104) will be described in greater detail below.

Figure 6:
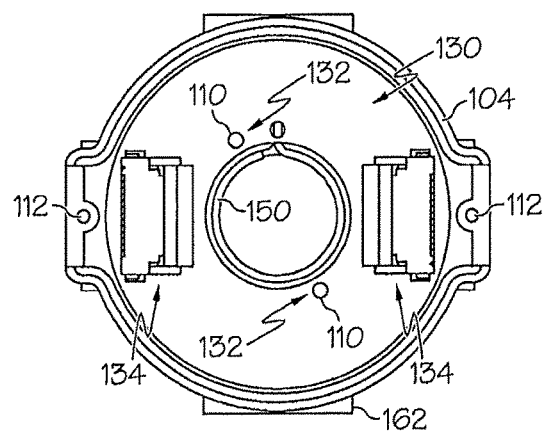
FIG. 6 depicts a top plan view of the electrode module of FIG. 4, with a top housing component and flex circuit component removed.
Figure 5:
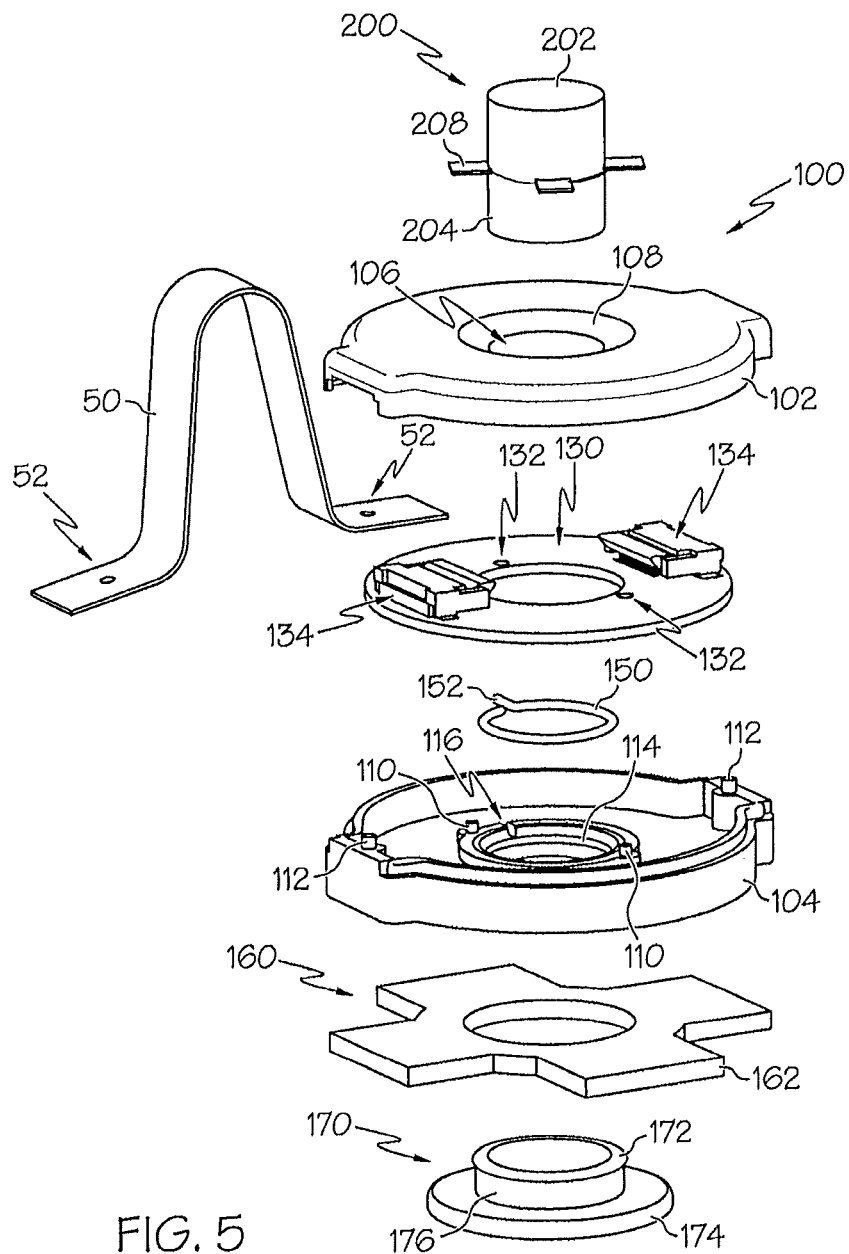
FIG. 5 depicts an exploded perspective view of the electrode module of FIG. 4, with an exemplary sensor.

Circuit board (130) of the present example comprises a pair of openings (132) and a pair of connectors (134). As shown in FIGS. 5-6, openings (132) of circuit board (130) are configured to align with and receive posts (110) of lower clamshell member (104). Openings (132) and posts (110) may thus assist in properly registering circuit board (130) with lower clamshell member (104) and assist in securing circuit board (130) relative to lower clamshell member (104). Of course, openings (132) and posts (110) are merely one of many different ways in which circuit board (130) may be registered and secured relative to lower clamshell member (104). Various other structures, features, techniques, etc. for registering and/or securing circuit board (130) relative to lower clamshell member (104) will be apparent to those of ordinary skill in the art in view of the teachings herein.

Figure 7:
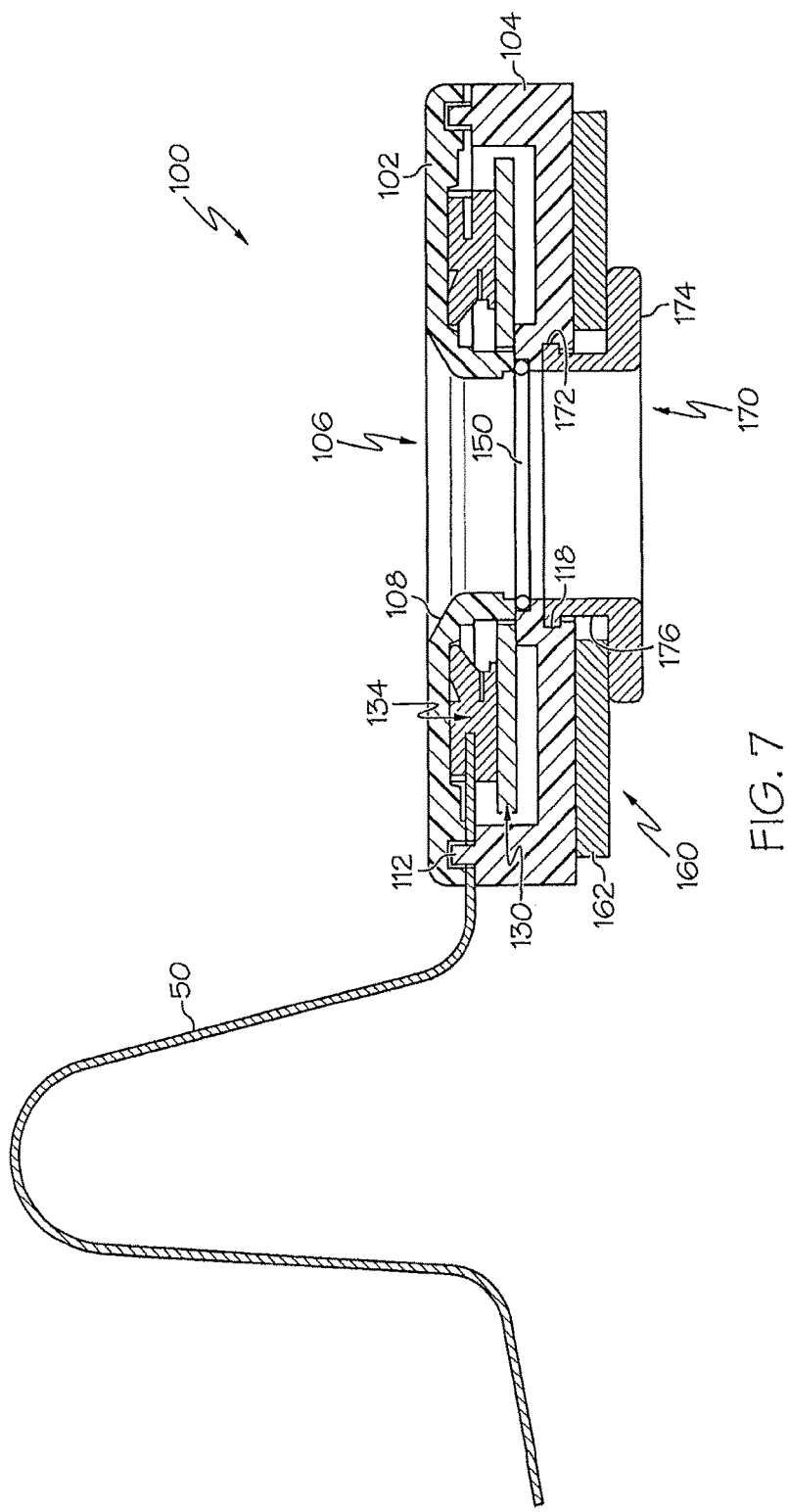
FIG. 7 depicts a cross-sectional side view of the electrode module of FIG. 4, taken along line 7-7 of FIG. 4.

Connectors (134) of circuit board (130) are configured to be physically and communicatively coupled with flexible connectors (50). In particular, each connector (134) has a slot that is configured to receive a free end of a corresponding flexible connector (50). Flexible connector (50) has an opening (52) that is configured to receive a post (112) of lower clamshell member (104). Thus, when flexible connector (50) is inserted in the slot of connector (134), with post (112) inserted through opening (52) of flexible connector (50), and when clamshell members (102, 104) are secured relative to each other as shown in FIG. 7, the insertion of post (112) through opening (52) may substantially prevent flexible connector (50) from being pulled out of connector (134). In addition, connector (134) may have one or more exposed/exposable electrical contacts within its slot; while the free end of flexible connector (50) may have one or more corresponding electrical contacts that are positioned to contact the one or more exposed/exposable electrical contacts within the slot of connector (134). Connector (134) may thus communicate power, commands, data, other signals, etc., to and/or from one or more traces of flexible connector (50). In some merely exemplary versions, it is contemplated that connectors (134), circuit board (130), flexible connector (50), and any other suitable components may have a unitary construction such that connectors (134), circuit board (130), and flexible connector (50) are in continuous communication with each other. In other merely exemplary versions, connectors (134), circuit board (130), and flexible connector (50) may be constructed from a rigid flex circuit. Other suitable constructions will also be apparent to one of ordinary skill in the art in view of the teachings herein.

Of course, connectors (134) are merely optional, and connectors (134) may be modified, substituted, supplemented, or omitted as desired. By way of example only, some alternative versions omit connectors (134) entirely by forming all flexible connectors (50) and circuit boards (130) as a single, unitary rigid-flex circuit. A merely illustrative example of such a rigid-flex circuit is disclosed in WIPO Publication No. 2011/0381103, entitled "Electrode System with Rigid-Flex Circuit," filed Sep. 23, 2010, the disclosure of which is incorporated by reference herein. Still other suitable ways in which connectors (134) may be modified, substituted, supplemented, or omitted will be apparent to those of ordinary skill in the art in view of the teachings herein.

As shown in FIGS. 1-3 and as noted above, electrode modules (100) are coupled via flexible connectors (50). In some versions, different electrode modules (100) have their own dedicated traces along such flexible connectors (50). Dedicated traces for a given electrode module (100) may run along part of the same length of flexible connectors (50) as dedicated traces for another given electrode module (100). For instance, a set of dedicated traces for one electrode module (100) may be provided on one layer of flexible circuitry in a given flexible connector (50); while a set of dedicated traces for another electrode module (100) may be provided on another layer of flexible circuitry on the same flexible connector (50), with both layers extending along a common length of the flexible circuitry of the same flexible connector (50). As another merely illustrative example, dedicated traces for one electrode module (100) may be provided on the same layer of flexible circuitry as dedicated traces for another electrode module (100), such that the separate sets of traces are geometrically parallel on a common layer. In some other versions, different electrode modules (100) may share one or more common traces in a given flexible connector (50). By way of example only, one or more traces in flexible circuitry of flexible connectors (50) may be used for bus transmissions, such that information associated with different electrode modules (100) may be combined onto a bus and communicated along one or more non-dedicated traces that are in communication with more than one electrode module (100). Various other suitable ways in which traces or other communication features may be used, provided, arranged, etc., will be apparent to those of ordinary skill in the art in view of the teachings herein.

Circuit board (130) in each electrode module (100) of the present example also comprises sensing circuitry (not shown), which includes an amplifier among other components. Such sensing circuitry is in communication with connectors (134) of circuit board (130), such that the sensing circuitry may communicate with the one or more traces of flexible connectors (50). With the sensing circuitry of circuit board (130) including an amplifier in the present example, it should be understood that electrode modules (100) are thus active. Such sensing circuitry may be configured and/or operable in accordance with the teachings of U.S. Pub. No. 2005/0215916, entitled "Active, Multiplexed Digital Electrodes for EEG, ECG, and EMG Applications," published Sep. 29, 2005, the disclosure of which is incorporated by reference herein; and/or in accordance with the teachings of any other document cited herein. Indeed, various ways in which the teachings herein may be combined with the teachings of U.S. Pub. No. 2005/0215916 and/or the teachings of any other document cited herein will be apparent to those of ordinary skill in the art. Alternatively, the sensing circuitry of circuit board (130) may have any other suitable configuration and/or operability. For instance, some versions of circuit board (130) may lack an amplifier, such that electrode modules (100) are not active. Still other suitable ways in which circuit board (130) may be configured, including but not limited to various forms and components of sensing circuitry, will be apparent to those of ordinary skill in the art in view of the teachings herein.

In the present example, conductive ring (150) comprises a tail portion (152) that extends radially outwardly. Conductive ring (150) is configured to rest on annular rim (114) of lower clamshell member (104), with tail portion (152) projecting through trench (116) of lower clamshell member (104). Accordingly, annular rim (114), trench (116), and tail portion (152) cooperate to assist in properly registering conductive ring (150) with lower clamshell member (104) and assist in securing conductive ring (150) relative to lower clamshell member (104). Of course, these features are just an example, and various other structures, features, techniques, etc. for registering and/or securing conductive ring (150) relative to lower clamshell member (104) will be apparent to those of ordinary skill in the art in view of the teachings herein. As best seen in FIG. 7, upper clamshell member (102) is positionable over conductive ring (150) to further secure conductive ring (150) in place by "sandwiching" conductive ring (150) between clamshell members (102, 104). As noted above, a portion of conductive ring (150) is still exposed in the inner diameter of the central opening (106) of the assembled electrode module (100) (e.g., when upper clamshell member (102) is secured to lower clamshell member (104), etc.). Conductive ring (150) is also communicatively coupled with the sensing circuitry of circuit board (130) (e.g., through contact via tail portion (152), etc.). In particular, conductive ring (150) is configured to communicate ERP signals to the sensing circuitry of circuit board (130) as will be described in greater detail below.

Electrode modules (100) may be coupled with head frame (24) in a variety of ways. In the present example, electrode modules (100) are coupled with head frame (24) through snap fittings at snap members (28) of head frame (24). For instance, as shown in FIGS. 5-7, each electrode module (100) of the present example is provided with a snap adapter (170). Each snap adapter (170) comprises an upper flange (172), a lower flange (174), and a cylindraceous portion (176) extending vertically between upper and lower flanges (172, 174). Lower clamshell member (104) includes an annular recess (118) that is configured to snappingly receive upper flange (172) of snap adapter (170) as shown in FIG. 7. Snap adapter (170) thus couples with electrode module (100) through a snap fitting in the present example, though it should be understood that any other suitable features, components, techniques, etc., may be used to secure a snap adapter (170) with an electrode module (100). Alternatively, electrode module (100) may have an integral or unitary snap adapter, or may couple with head frame (24) in some other way.

In the present example, a pad (160) is secured to each snap adapter (170). Each pad (160) has a plurality of outwardly extending tabs (162) and is relatively soft. For instance, the configuration of pad (160) may reduce discomfort to a test subject when a clinician manipulates electrode modules (100) while electrode modules (100) are on the test subject's head. Pad (160) is configured to fit about cylindraceous portion (176) of snap adapter (170). As shown in FIG. 7, pad (160) is "sandwiched" between the lower surface of lower clamshell member (104) and the upper surface of lower flange (174). Of course, pad (160) may be coupled with electrode module (100) in a variety of other ways. By way of example only, pad (160) may be secured to electrode module by one or more clips, hook and loop fasteners, adhesives, etc. Alternatively, pad (160) may be omitted entirely. For instance, snap member (28) of head frame (24) may be positioned about cylindraceous portion (176) of snap adapter (170). Snap member (28) may thus be "sandwiched" between the lower surface of lower clamshell member (104) and the upper surface of lower flange (174), similar to pad (160) in FIG. 7. In the present example, however, snap adapter (170) snappingly engages with snap member (28) (e.g., such that at least a portion of snap member (28) is positioned below lower flange (174)).

As yet another merely illustrative variation, snap adapter (170) may simply be omitted. By way of example only, snap member (28) may itself snappingly engage with lower clamshell member (104). For instance, snap member (28) may include an outwardly extending annular flange that is snappingly received in annular recess (188) of lower clamshell member (104). As still another merely illustrative variation, electrode modules (100) may couple directly with head frame (24), such that no snap fittings are used to couple electrode modules (100) with head frame (24). By way of example only, electrode modules (100) may be coupled with head frame (24) by one or more clips, hook and loop fasteners, adhesives, etc. In addition, while electrode modules (100) are removably coupled with head frame (24) in the present example, electrode modules (100) may be permanently affixed to head frame (24) in some other versions.

It should also be understood that when several snap member (28) (or other types of electrode module (100) engagement structures) and resilient straps (26) are arranged to provide a head frame (24), some snap members (28) may not have a corresponding electrode module (100) coupled thereto. It should therefore be understood that some headsets (20) may be configured to accommodate different kinds of electrode systems that have different numbers of and/or arrangements of electrode modules (100), providing a degree of modularity. Still other suitable ways in which electrode modules (100) may be incorporated into a headset (20) will be apparent to those of ordinary skill in the art in view of the teachings herein.

E. Exemplary Sensors

Figure 8:
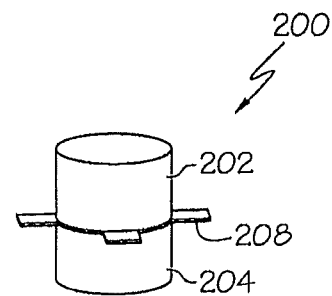
FIG. 8 depicts a perspective view of an exemplary sensor for use with the ERP testing system of FIG. 1.
Figure 9:
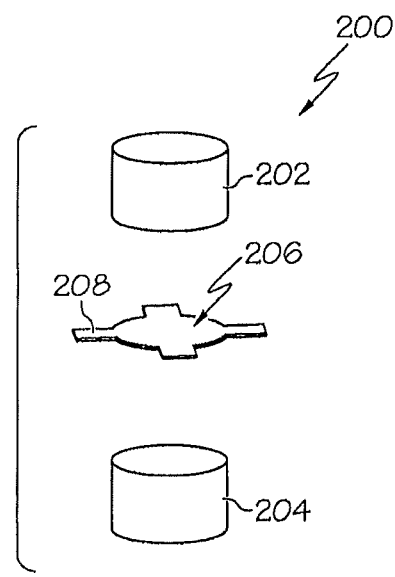
FIG. 9 depicts an exploded view of the sensor of FIG. 8.

As shown in FIGS. 5 and 8-9, electrode system (10) of the present example further includes removable sensors (200). Removable sensors (200) of this example each comprise an insulating upper portion (202), an electrolytic hydrogel lower portion (204), and a conductive center portion (206) positioned between upper and lower portions (202, 204). Conductive center portion (206) comprises a plurality of outwardly extending conductive tabs (156). Each sensor (200) is configured to be inserted in the central opening (106) of a corresponding electrode module (100) and fit snugly therein. In some settings, each electrode module (100) in an electrode system (10) has an associated removable sensor (200) inserted therein; though some electrode modules (100) may lack an associated electrode module (100) in some settings. Inclined surface (108) of upper clamshell member (102) at the perimeter of opening (106) may facilitate insertion of sensor (200) in opening (106), such as by guiding sensor (200) into opening. Of course, as with other features described herein, inclined surface (108) is merely optional, and may be modified, substituted, supplemented, or omitted as desired.

When removable sensor (200) is inserted in electrode module (100), and the corresponding head frame (24) is secured to a test subject's head, removable sensor (200) is configured such that electrolytic hydrogel lower portion (204) contacts the scalp of the test subject. For instance, sensor (200) may have a height such that hydrogel lower portion (204) protrudes below lower flange (174) of snap adapter (170) while insulating upper portion (202) is vertically positioned at or near inclined surface (108) of upper clamshell member (102). Alternatively, sensors (200) may have any other suitable dimensions. Furthermore, depending on the positioning of a given electrode module (100), the associated electrolytic hydrogel lower portion (204) may contact some other part of the test subject's head or body. For instance, hydrogel lower portion (204) may simply contact the hair on the test subject's head; and electrode system (10) may still work properly even if sensors (200) only contact the hair on the test subject's head without necessarily contacting the skin on the test patient's scalp. Due to the electrolytic properties of the electrolytic hydrogel lower portion (204), electrolytic hydrogel lower portion (204) may pick up voltages or signals (e.g., ERP signals, etc.) from the test subject's (e.g., patient's) skin. Electrolytic hydrogel lower portion (204) may collect data without needing to be pasted or glued to the test subject's head, as the hydrogel itself may sufficiently adhere to the subject's head while also allowing removable sensor (200) to be pulled away from the subject's head with relative ease.

As noted above, tabs (208) of the present example are formed as unitary extensions of a conductive member (206) that is disposed between insulating upper portion (202) and electrolytic hydrogel lower portion (204). Conductive member (206) and tabs (208) are configured such that tabs (208) are resiliently biased to assume radially outwardly extending orientations, as shown in FIGS. 5 and 8-9. It should be understood that when sensor (200) is inserted in opening (106) of electrode module (100), tabs (208) contact conductive ring (150), which is exposed in the inner diameter of opening (106) as shown in FIG. 7. For instance, tabs (208) may resiliently bear against conductive ring (150) when sensor (200) is inserted in opening (106). Such contact between tabs (208) and conductive ring (150) may provide a path for communication from conductive member (206) to conductive ring (150) as described in greater detail below. In addition, elastomeric properties or other properties of insulating upper portion (202) and/or hydrogel lower portion (204) may help retain sensor (200) in opening (106) of electrode module. In addition or in the alternative, sensor (200) may be oversized relative to opening (106), such that sensor (200) is snugly or interferingly fit in opening (106). Other ways in which sensor (200) may be substantially retained in opening (106) will be apparent to those of ordinary skill in the art in view of the teachings herein.

Conductive member (206) and tabs (208) may be formed of silver-silver chloride and/or any other suitable material or materials. Conductive ring (150) may also be formed of silver-silver chloride and/or any other suitable material or materials. With conductive member (206) and tabs (208) being in direct contact with electrolytic hydrogel lower portion (204), it should be understood that voltages or signals that are picked up by electrolytic hydrogel lower portion (204) may be further communicated to and through tabs (208). With tabs (208) being in contact with conductive ring (150) when sensor (100) is inserted in opening (106) of electrode module (100), tabs (208) may thus communicate voltages or signals picked up by electrolytic hydrogel lower portion (204) to conductive ring (150), which may in turn communicate such voltages or signals to sensing circuitry of circuit board (130). An amplifier on circuit board (130) (or elsewhere) may amplify the signal, and other components within the sensing circuitry may perform other processing of the signal if desired, and the signal may then be communicated away from electrode module (100) via flexible circuitry in one or more flexible connectors (50). The signals may thus ultimately be communicated to control box interface module (30) via flexible connectors (50) and then on to control box (40) via cable (42).

In some versions, removable sensors (200) comprise HydroDot® Disposable EEG Electrodes or HydroDot® Biosensors by HydroDot, Inc. of Westford, Mass. Various aspects of the HydroDot® Disposable EEG Electrode Application System are discussed in U.S. Pat. No. 5,479,934, entitled "EEG Headpiece with Disposable Electrodes and Apparatus and System and Method for Use Therewith," issued Jan. 2, 1996, which is incorporated by reference herein. Of course, various components of electrode system (10), including but not limited to removable sensors (200), may be configured, modified, and/or operable in accordance with any suitable teachings in U.S. Pat. No. 5,479,934. Indeed, various ways in which the teachings herein may be combined with the teachings of U.S. Pat. No. 5,479,934 will be apparent to those of ordinary skill in the art. It should also be understood that removable sensors (200) are not necessarily required in all versions. For instance, electrode modules (100) may be configured such that they have an electrical interface with the test subject's head and/or some other type of interface with the test subject's head and/or other body part through an injectable gel or in any other suitable fashion.

While sensors (200) of the present example have a substantially cylindraceous shape, it should be understood that sensors (200) may alternatively have any other shape. By way of example only, sensors (200) may have a cubical shape, a right cuboidal shape, a conical shape, a frustoconical shape, a pyramidal shape, a spherical shape, and/or any other suitable shape. Similarly, while conductive rings (150) of the present example have a substantially circular shape, it should be understood that conductive rings (150) may alternatively have any other shape. By way of example only, conductive rings (150) may have a square shape, a rectangular shape, a triangular shape, and/or any other suitable shape. Still other suitable configurations of and relationships between sensors (200) and conductive rings (150) will be apparent to those of ordinary skill in the art in view of the teachings herein.

In the present example, electrode system (10) comprises eight electrode modules (100). As another merely illustrative example, electrode system (10) may comprise twenty three electrode modules (100). Of course, electrode system (10) may alternatively comprise any other suitable number of electrode modules (100). It should also be understood that electrode modules (100) may be arranged in a variety of ways. By way of example only, various suitable arrangements are disclosed in the documents that are cited herein.

Signals obtained using electrode system (10) may be processed in accordance with the teachings of U.S. Pub. No. 2008/0208072, entitled "Biopotential Waveform Data Fusion Analysis and Classification Method," published Aug. 28, 2008, the disclosure of which is incorporated by reference herein. In addition or in the alternative, signals obtained using electrode system (10) may be processed in any other suitable fashion, including but not limited to the manner described in greater detail below. In addition, various suitable ways in which electrode system (10) may be used (including but not limited to signal processing) are disclosed in the various documents cited herein. Still other suitable ways in which electrode system (10) may be used will be apparent to those of ordinary skill in the art in view of the teachings herein. It is contemplated that the teachings herein may be incorporated into or otherwise combined with the systems, components, and methods disclosed in the documents cited herein, in numerous ways. Suitable ways in which the teachings herein may be incorporated into or otherwise combined with the teachings of the documents cited herein will be apparent to those of ordinary skill in the art in view of the teachings herein.

In addition to or as an alternative to having any or all of the components, features, configurations, and/or operabilities described above, an ERP system may have any or all of the components, features, configurations, and/or operabilities described in U.S. Provisional Patent Application Ser. No. 61/381,569, entitled "Electrode System with In-Band Impedance Detection," filed Sep. 10, 2010, the disclosure of which is incorporated by reference herein. Still other suitable components, features, configurations, and/or operabilities for an ERP system will be apparent to those of ordinary skill in the art in view of the teachings herein.

II. Exemplary Biomarker Fusion System

Figure 10:
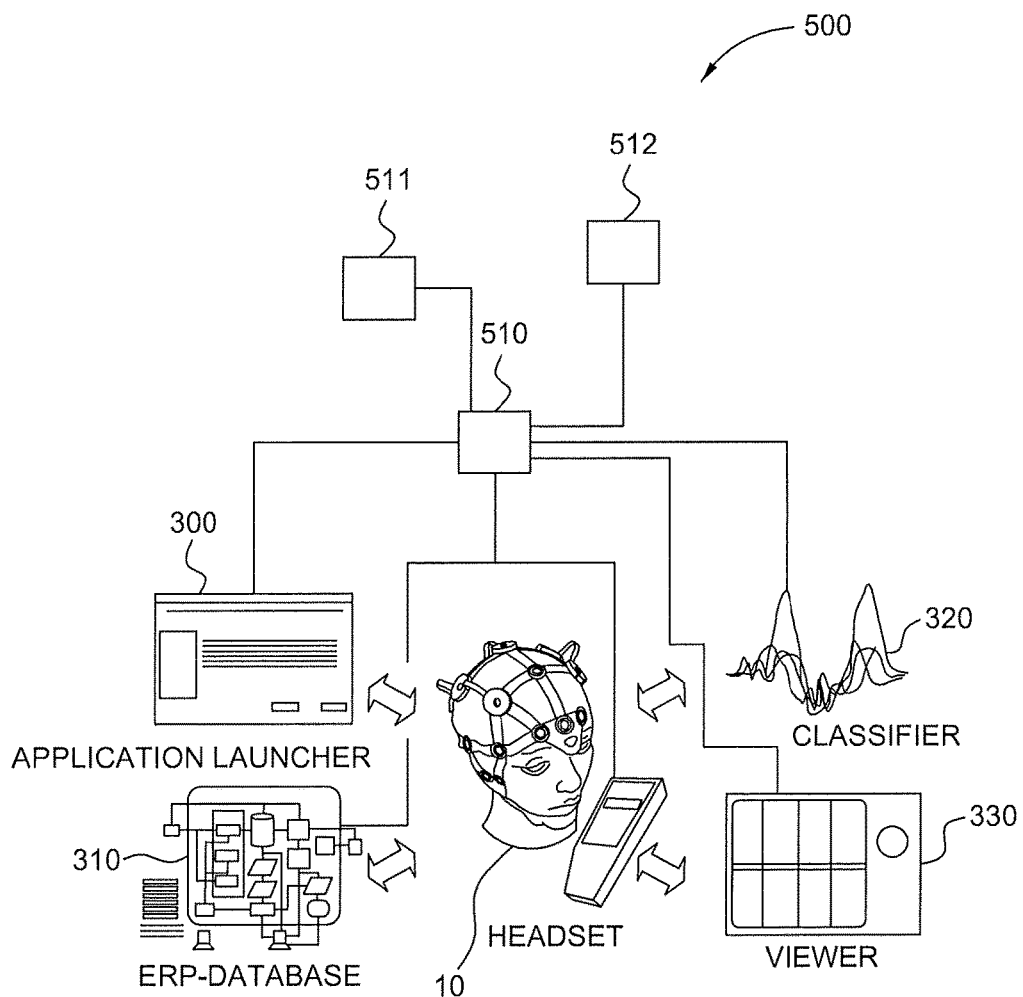
FIG. 10 depicts a diagrammatic view of an exemplary ERP testing system.

FIG. 10 shows an exemplary ERP system (500) comprising an exemplary electrode system (10) as shown in FIGS. 1-9 in communication with a launcher (300), a database (310), a classifier (320), and a viewer (330). It will be appreciated that various kinds of features that may be included in ERP system (500), including features not described herein. Furthermore, only some of the features described herein are included in some versions of ERP system (500). Generally, ERP system (500) includes a software application (510) that is both configured for use with headset (20) and in communication with launcher (300), database (310), classifier (320), and viewer (330). To that end, the software application (510) may be a client or a server application used to create and administer new accounts, users, groups, and headsets (20) in connection with ERP testing. Furthermore, ERP system (500) is operable to create and store test protocols using high-level, paradigm-specific parameters. Software application (510) of ERP system (500) is operable to store patient data, which will be discussed in more detail below. Software application (510) of ERP system (500) may also be used at or in conjunction with a testing clinic to administer test protocols. ERP system (500) may utilize a control box (40), as seen in FIG. 1, to administer a desired test where control box (40) has a test protocol installed. In the exemplary version, control box (40) comprises a handheld control unit (HCU), but any suitable form factor for control box (40) may be used as would be apparent to one of ordinary skill in the art in view of the teachings herein. Once test protocols are carried out, software application (510) of ERP system (500) allows users to view and analyze the results of an ERP test and may also be used with a computer (511) to view and analyze results.

As stated above, ERP system (500) includes software application (510) operable to create and administer new accounts, users, groups, and headsets (20). It will be appreciated that as users and accounts are created in software application (510), users may be able to have more than one account on the application. The users and/or accounts may be controlled such that specific account users or accounts have access limited to other applications or data. Furthermore, users and/or accounts on software application (510) may be organized into groups operable to facilitate sharing of ERP test protocols, test configurations, test data, and other anonymous patient data. Headsets (20) may also be used in conjunction with software application (510) to register, detect, self-test, or reorder headsets (20).

As also stated above, ERP system (500) includes software application (510) operable to create and store test protocols using high-level, paradigm-specific parameters. In particular, ERP system (500) is sufficient to carry out a complete set of predefined tests during a single testing session. In order to do so, it will be appreciated that the test protocol stored on control box (40) contains a complete set of ERP paradigm descriptions, a sufficient set of control parameters, control logic, and other necessary information for control box (40) to run a complete set of predefined tests. ERP system (500) is further highly customizable. The user may define tests to be performed by ERP system (500) during a single session. Furthermore, since some of the tests carried out by ERP system (500) include audio stimulus, ERP system (500) is operable to perform an audiometry test prior to the administration of ERP tests.

In some versions, ERP system (500) may be coupled with a biomarker fusion system (512). In the present example, biomarker fusion system (512) is operable to process biomarker related data associated with a particular patient/subject, such as by comparing that particular patient's/subject's data against historical data associated with other patients/subjects, and determine which class of patients/subjects the particular patient/subject is most like. In addition to identifying the class that the particular patient/subject most likely belongs to, biomarker fusion system (512) may determine and communicate how close the particular patient/subject is to the identified class. By way of example only, when biomarker fusion system (512) is used to determine whether a particular patient/subject most likely belongs to Class A (e.g., patients with Alzheimer's) or Class B (e.g., patients without Alzheimer's), biomarker fusion system (512) may determine and communicate to the user that there is a 90% likelihood that the particular patient/subject belongs to Class A In the context of ERP system (500), ERP test results may be communicated into biomarker fusion system (512) where the test results are fused and/or otherwise processed with other biomarker data (and/or various other data) to assist in classifying a test subject (e.g., to diagnose a medical condition associated with a combination of biomarkers expressed by the test subject, etc.). In addition or in the alternative, ERP test results and/or related data communicated into biomarker fusion system (512) may be used to refine associations previously established between certain combinations of other biomarker expressions/parameters and certain medical conditions. Still further in addition or in the alternative, data within biomarker fusion system (512) may be used to assist in selecting an ERP testing protocol before the ERP test is conducted, based on one or more biomarker expressions/parameters associated with the test subject and/or based on other factors. In some instances, biomarker fusion system (512) may be used without involving ERP system (500) or ERP testing at all. It should therefore be understood that the present disclosure of biomarker fusion system (512) in the context of ERP system (500) is merely illustrative. It is contemplated that these two systems (500, 512) may be completely separate, independent, unrelated, etc.

It will be appreciated that data relating to biomarkers associated with patients/subjects may have several different applications. For example, in some applications, analysis of biomarkers may be used to identify subjects that are at a higher than normal risk for developing a disease. Biomarkers may also be used to identify early disease in asymptomatic patients. In yet other applications, biomarkers may be used to determine which self-selecting subjects have an ongoing disease process outside of the normal neurological spectrum. Furthermore, biomarkers may be used to differentiate between diseases with similar clinical presentations but that may have different histopathologies. A physician or other user may use biomarkers to determine the severity of stage of a disease. In yet other exemplary versions, biomarkers can determine which group of pathologic patients can benefit from a particular therapy. In yet other instances, it will be understood that biomarkers may be used to develop a measure which demonstrates the desired pharmacodynamic effect on treated patients or to develop a measure which demonstrates the desired symptomatic effect on treated patients. While the above-listed applications for biomarkers provide some exemplary uses of biomarkers, it will be understood that the above applications are merely exemplary and not necessarily exhaustive. It is contemplated that biomarkers may be used in any suitable manner as would be apparent to one of ordinary skill in the art in view of the teachings herein.

It will be appreciated that that any reference to a "biomarker" may include any associated characteristic about a human being including personal information, phenotype, lab tests, psychometric evaluations, imaging results of the test subject, bioelectric characteristics, metabolic characteristics, behavioral characteristics, molecular or biochemical characteristics, anatomical characteristics, medical history information, family history information, event-related potentials, imaging findings, medications, prescription names, dosage information for medication taken by the patient, dates of any prescription medications taken, or any other suitable information as will be apparent to one of ordinary skill in the art in view of the teachings herein.

In versions where ERP system (500) is in communication with a database of information, biomarker fusion system (512) may also be in communication with that database. The use of the term "database" in this regard should not be read as requiring any particular arrangement, format, or relationship of data. "Database" is instead intended to generically refer to stored information—whether on a single storage device, several storage devices, or otherwise, which may be locally or remotely located. In addition or in the alternative, ERP system (500) may be in communication with a biomarker fusion database. In addition or in the alternative, where ERP system (500) includes a web portal to information (e.g., to ERP testing protocols, test subject data, ERP test results, etc.), such a web portal may also provide access to at least some parts of biomarker fusion system (512) and/or a means to upload biomarker related information to biomarker fusion system (512), including ERP related information and/or non-ERP related information (e.g., patient identifying information, account information, etc.), etc.

The following describes one merely illustrative way in which biomarker fusion system (512) may be carried out. It should be understood, however, that it is contemplated that biomarker fusion system (512) may be carried out in various other ways. It is also contemplated that biomarker fusion system (512) may be carried out in a way that is independent of any ERP system (500). Therefore, reference to ERP systems (500) and methods herein should not be read as requiring biomarker fusion system (512) to necessarily have a relationship with ERP system (500) or method.

Figure 11:
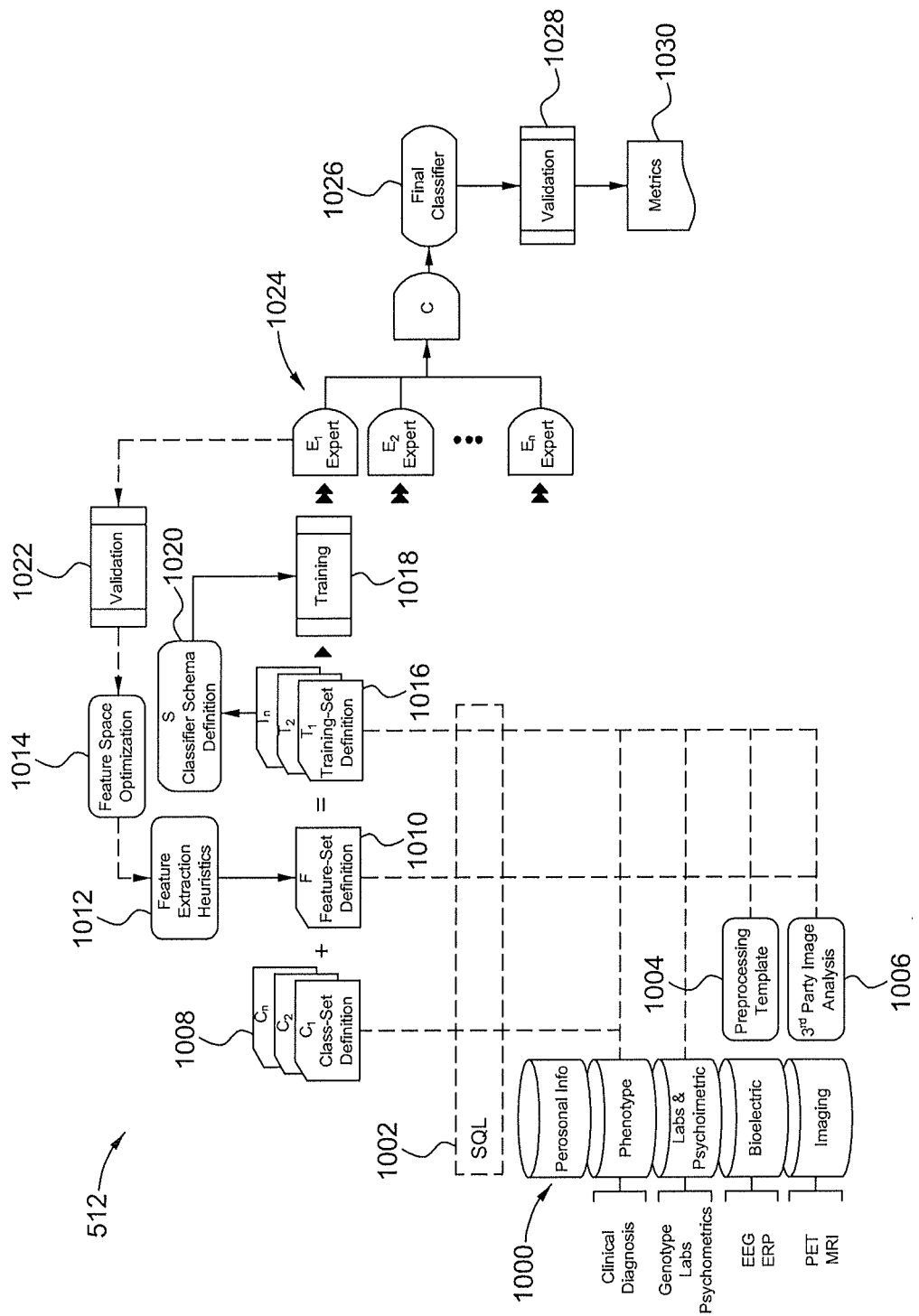
FIG. 11 depicts a diagrammatic view of an exemplary biomarker fusion system.

In the exemplary version, and as shown in FIG. 11, biomarker fusion system (512) comprises a class set definition module (1008), a feature set definition module (1010), and a training set definition module (1016). Class set definition module (1008) works in conjunction with feature set definition module (1010) to form a training set definition module (1016), which will be described in more detail below. It will be appreciated that biomarker fusion system (512) may be used to form a "meta-model." A meta-model used in this context should be understood to include a high level model using a set of biomarker variables with other biomarker variables to understand a correlation between the various biomarker variables. A meta-model may also include the analysis, construction, and development of the frames, rules, constraints, models, and theories applicable and useful for analyzing a predefined class of problems. An exemplary process for forming a meta-model will be described in further detail below.

As mentioned above, biomarker fusion system (512) comprises a biomarker database (1002). In the present example, biomarker database (1002) is stored in a SQL-based database, but it will be appreciated that any suitable type of database may be used as would be apparent to one of ordinary skill in the art in view of the teachings herein. Biomarker database (1002) is operable to store biomarker information (1000). As mentioned above, biomarker information (1000) may include personal information, phenotype information (as a result of, for example, clinical diagnoses, etc.), lab tests results and psychometric information (as a result of, for example, psychometrics, lab tests and genotype information, etc.), bio-electric information (as a result of, for example, electro-encephalogram and evoked response potential tests, etc.), and imaging information (as a result of, for example, MRI and PET testing, etc.). It will be appreciated that other types of biomarkers may be stored as biomarker information (1000) as would be apparent to one of ordinary skill in the art in view of the teachings herein. In some versions, biomarker data is entered manually into biomarker database (1002). In addition or in the alternative, biomarker data may be communicated automatically into biomarker database (1002) (e.g., by another system, etc.). In some instances, a user or system may input raw biomarker data into biomarker fusion system (512), and biomarker fusion system (512) may be operable to convert that raw data into a standardized form, remove noise, and/or perform other processing on the data before entering it into biomarker database (1002).

In the present example, it is also understood that personal information may be stored securely or in an encrypted manner such that access to biomarker information (1000) includes hiding personal information of the patients/subjects. In some exemplary versions, the personal information may be accessible or hidden based on a particular access level of the user. Additionally, in some exemplary versions, personal information may be hidden and/or accessible based on a setting or selection regarding a particular patient or subject. In other words, a user of biomarker fusion system (512) may simply mark a particular patient as being private or secured. In yet other exemplary versions, it will be appreciated that biomarker information (1000) may be de-identified such that the information remains intact, but personal information of the patient or subject is removed such that the biomarker information (1000) cannot be specifically matched with a patient/subject. In yet other exemplary versions, different levels of security and/or encryption may be applied based on the type of biomarker information itself. Furthermore, it will be appreciated that in some circumstances, different patients may have different biomarker information available. In some such instances, biomarker fusion system (512) is operable to fill in the missing information with temporary information if particular biomarker information is needed in, for example, forming a training set definition. For example, if a particular piece of biomarker information is missing, biomarker fusion system (512) can opt to temporarily use an average value of all of the patients/subjects in the same group for the particular biomarker. Other suitable ways of temporarily filling in missing information may be used as would be apparent to one of ordinary skill in the art in view of the teachings herein.

Biomarker fusion system (512) further comprises a preprocessing template (1004) and a third party image analysis module (1006). In the exemplary version, preprocessing template (1004) and third party analysis module (1006) are in communication with biomarker information (1000). Preprocessing template (1004) is operable to take any raw information stored in biomarker information (1000) and perform any suitable transformation as would be apparent to one of ordinary skill in the art in view of the teachings herein. For example, preprocessing template (1004) may be operable to normalize information, or convert the units or scale of any information stored in biomarker information (1000). Once stored in biomarker fusion system (512), preprocessing template (1004) may be automatically applied to all biomarker data of the same type.

Third party data analysis (1006) may include any type of data analysis software or module. For instance, third party data analysis (1006) may be used to analyze PET images, MRI images, ultrasound images, other types of imaging data, and/or other types of non-imaging data, etc. By way of example only, third party data analysis (1006) may rely on the resources, processing, expertise, etc. of a third party to analyze such data from the biomarker information (1000). It will be appreciated that third party data analysis (1006) may be operable to utilize raw imaging data stored in biomarker information (1000). In addition or in the alternative, third party data analysis (1006) may be operable to utilize raw imaging data after the raw imaging data has undergone processing at preprocessing template (1004). It should also be understood that preprocessing template (1004) and/or third party data analysis (1006) may be accessible through a wizard or any other suitable interface, which may be incorporated into the user interface described below.

Biomarker database (1002) is also in communication with class set definition module (1008) and feature set definition module (1010). Class set definition module (1008) is operable to define a class set based on any variable present in biomarker information (1000), such that a group of patients/subjects within a defined class set have some aspect of phenotype in common with each other. For example, one class set formed by class set definition module (1008) may be based on height related criteria and may include patients and/or subjects having a height of less than 6 ft. As another merely illustrative example, a class set definition could be based on a particular test result from a lab test (e.g., value of test results falling within a certain range, etc.). As will be seen below in the discussion of an exemplary user interface, any suitable biomarker variables may be selected to define a class set through class definition module (1008). It should also be understood that, in the present example, at least two class sets (that are based on different criteria) must be defined through class set definition module (1008). This will enable biomarker classification system (512) to identify which one of the at least two defined class sets a particular patient/subject most likely belongs in, based on correlations as described in greater detail below.

It is also contemplated that a class set may be further limited or defined based on a time/age component. For example, in the case where a class set is defined to include subjects having a height of less than 6 ft., a time component may be used to filter the results to only include subjects having a height of less than 6 ft. at a particular age or at some other point in time. As another merely illustrative example, a time/age limitation may be used to define a class set based on patients/subjects having a certain type of test score falling within a certain range when the patients/subjects were over 60 years of age. Other suitable types of time/age restrictions will be apparent to those of ordinary skill in the art in view of the teachings herein.

Feature set definition module (1010) is operable to define a feature set based on additional biomarker criteria selected from biomarker information (1000). For example, a particular lab test result (or a particular range of lab test results, etc.) may be selected in the feature set definition module (1010). Feature set definition module (1010) may be used to select a biomarker in its raw form or may use biomarkers after being processed by preprocessing template (1004) and/or third party data analysis (1006). In some versions, the criteria/variables that are used to define a feature set in feature set definition module (1010) do not have a known or apparent relationship with the criteria/variables that were used to define the class sets in class set definition module (1008). For instance, since height and weight are known to have a relationship, it may be desirable to define a feature set that is not based on weight when one of the class sets is based on height. Of course, any suitable criteria may be used to define a feature set in feature set definition module (1010).

Biomarker fusion system (512) is ultimately operable to determine which particular features in a defined feature set are most likely to distinguish one class of patients/subjects from another class of patients/subject. For instance, biomarker fusion system (512) may be operable to automatically determine that one or more particular features tend to indicate that a patient/subject has Alzheimer's, while another one or more particular features tend to indicate that a patient/subject does not have Alzheimer's. This can be done by analysis of various permutations of features expressed by patients/subjects known to have Alzheimer's against various permutations of features expressed by patients/subjects that do not have Alzheimer's.

Once class set definition (1008) and feature set definition (1010) have been selected, class set definition (1008) and feature set definition (1010) are combined, as shown in FIG. 11 to form training set definition (1016). As a result, training set definition (1016) comprises instructions to biomarker fusion system (512) to identify patients/subjects matching each class set definition (1008), then to extract features from those identified patients/subjects based on the feature set definition (1010). Biomarker fusion system (512) is operable to ensure that the features used to form feature set definition (1010) are not also used to form the class set definitions (1008), since training classifiers with overlaps in these features and definitions (1008, 1010) may result in redundant classifications.

In the exemplary version, training set definition (1016) is provided to classifier schema definition (1020), which then leads to training module (1018). In yet other exemplary versions, training set definition (1016) may be provided directly to training module (1018). Training module (1018) is operable to utilize two or more training set definitions (1016). Classifier schema definition (1020) is also operable to utilize two or more training set definitions (1016). It will be appreciated that classifier schema definition (1020) may be operable to apply an algorithm to compile the various training set definitions (1016). Thus, as training set definitions (1016) are provided to classifier schema definition (1020), they help define classifier schema definition (1020) and are thereafter sent to training module (1018). In some exemplary versions, training module (1018) is operable to determine various relationships and correlations between biomarkers selected from biomarker database (1002).

Figure 12:
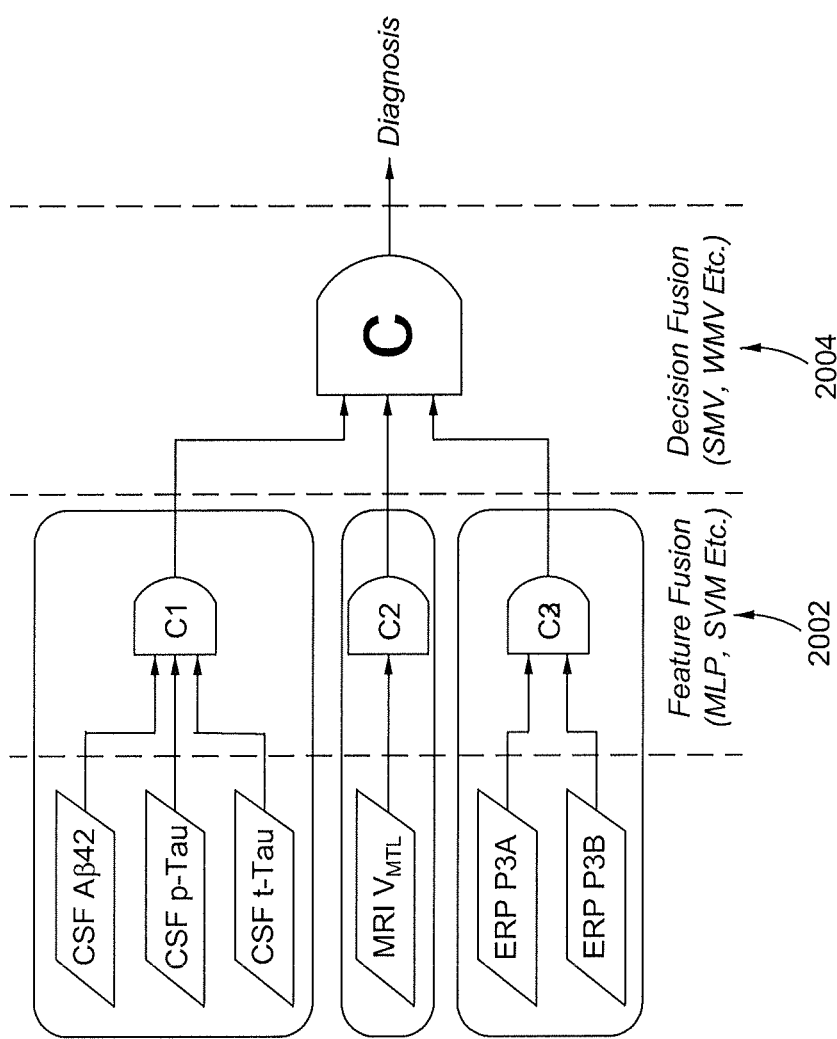
FIG. 12 depicts a diagrammatic view of an exemplary biomarker fusion method.

Training module (1018) then leads to expert classifier module (1024), which is operable to use training set definition (1016) to make a decision and/or diagnosis about a patient exhibiting one of the biomarkers used in class set definition (1008) or feature set definition (1010). For example, FIG. 12 shows an illustrative example of how various kinds of biomarker data may be fused and processed to render a diagnosis of a patient as might occur in expert classifier module (1024). In this example, there are three biomarker data points relating to cerebrospinal fluid levels, one biomarker data point relating to biomarker data obtained through magnetic resonance imaging (MRI), and two biomarker data points relating to biomarker data obtained through ERP testing. In the depicted example, there are two fusion stages. In the first stage (2002), the cerebrospinal fluid data points are fused with each other and the ERP data points are fused with each other. By way of example only, this data fusion may include Bayes, Support Vector Machines (SVM), or various other kinds of classification algorithms. By fusing the data points within each data type, biomarker fusion system (512) makes separate determinations, based on data type, to identify which class the patient/subject most likely belongs to. For instance, in "C1," biomarker fusion system (512) determines which class the patient/subject most likely belongs to based on the cerebrospinal fluid data. In "C2," biomarker fusion system (512) determines which class the patient/subject most likely belongs to based on MRI data. In "C3," biomarker fusion system (512) determines which class the patient/subject most likely belongs to based on ERP testing data. In the present example, these determinations (C1, C2, C3) are carried out independent of each other at first stage (2002).

It should be understood that the accuracy of a classification algorithm used at first stage (2002) may vary based on the type of data, such that the particular classification algorithm to use for a given data set may be selected based on the accuracy of that algorithm in the context of that type of data. For instance, the classification algorithm preferred for MRI data may not be preferred for cerebrospinal fluid data. Thus, the "C1," C2," and "C3" shown in first stage (2002) may be viewed as an expert in each type of data providing their own opinion on how best to fuse the features/data within their type of data should be interpreted (e.g., identifying which class the patient/subject most likely belongs to based on the data within the expert's type). In some versions, the user is able to select which type of classification algorithm to use (e.g. based on data type or otherwise). In addition or in the alternative, biomarker fusion system (512) may automatically select a preferred type of classification algorithm to use (e.g. based on data type or otherwise). In the present example, the term "fused data" in the context of first stage (2002) refers to the determinations (C1, C2, C3) made by biomarker data fusion system (512) at first stage (2002).

In a second stage (2004), the fused cerebrospinal fluid data (C1), the MRI data (C2), and the fused ERP data (C2) are all fused and otherwise processed to render a diagnosis. By way of example only, this may include simply using a "majority rule" type of processing of C1, C2, and C3. For instance, if C1 and C2 indicate that the patient/subject most likely belongs in the Alzheimer's class while C3 indicates that the patient/subject most likely belongs in the non-Alzheimer's class, the result of second stage (2004) may simply be an indication that the patient/subject most likely belongs in the Alzheimer's class, based on the fact that two out of three "experts" made that determination in first stage (2002). As another merely illustrative example, biomarker fusion system (512) may place more weight on certain "experts" of the first stage (2002) versus other "experts" of the first stage (2002), such that second stage (2004) employs a weighted majority rule approach when analyzing the results of first stage (2002) to determine which class the patient/subject most likely belongs to. Various other suitable ways in which fusion/processing may be provided and carried out in each stage (2002, 2004) will be apparent to those of ordinary skill in the art in view of the teachings herein. It should also be understood that, in some versions, the first fusion stage may be eliminated, such that all six of the original data points are fused/processed simultaneously together in a single state. Of course, data may be fused/processed in numerous other ways, including but not limited to in additional stages, different combinations/permutations, etc.

Returning back to FIG. 11, validation module (1022) is in communication with expert classifier module (1024) and is in communication with featurespace optimization module (1014). The diagnosis from expert classifier module (1024) is sent to validation module (1022) where validation module performs an algorithm or verification step to determine the quality of the diagnosis provided by expert classifier module (1024). Various validation algorithms such as k-fold validation, shuffle validation, and/or other suitable algorithms may be provided as will be apparent to those of ordinary skill in the art in view of the teachings herein. In some exemplary versions, it will be appreciated that validation module (1022) need not be used. Validation module (1022) leads to featurespace optimization module (1014), which leads to feature extraction heuristics (1012). Featurespace optimization module (1014) and feature extraction heuristics (1012) are operable to determine, wither through automated algorithms or through explicit user input, the optimal feature(s) and/or appropriate combinations of features to achieve desired classification performance. It will be appreciated that the user may also provide feedback based on information outside of biomarker fusion system (512) to aid in determining the accuracy of the recommended diagnosis by expert classifier module (1024). It will be appreciated that validation module (1022), featurespace optimization module (1014), and feature extraction heuristics (1012) are thus operable to provide a feedback mechanism for feature set definition module (1010). In other exemplary versions, biomarker fusion system (512) may lack such a feedback mechanism.

Expert classifier module (1024) sends a recommended diagnosis to final classifier (1026) where the diagnosis is sent to validation module (1028) followed by sending the results to metrics module (1030). Validation module (1028) is operable to allow the user to determine whether the quality of the trained classifier is acceptable. Metrics module (1030) is operable to present metrics regarding the quality of classification performed by individual experts as well as the overall classifier. In some exemplary versions, metrics module (1030) is operable to output the overall accuracy, sensitivity, specificity, positive predictive value (PPV), and/or negative predictive value (NPV) of the results.

III. Exemplary User Interface for Biomarker Fusion System

Biomarker fusion system (512) may be used in a variety of scenarios. It will be appreciated that the following user interface presents a merely illustrative version of a user interface for biomarker fusion system (512). It is contemplated that other suitable user interfaces may be used as would be apparent to one of ordinary skill in the art in view of the teachings herein. Indeed, it is understood that other user interface may be used without departing from the scope and spirit of biomarker fusion system (512). The user interfaces of FIGS. 13-32 may be used at various stages of the process shown in FIG. 11.

Figure 13:
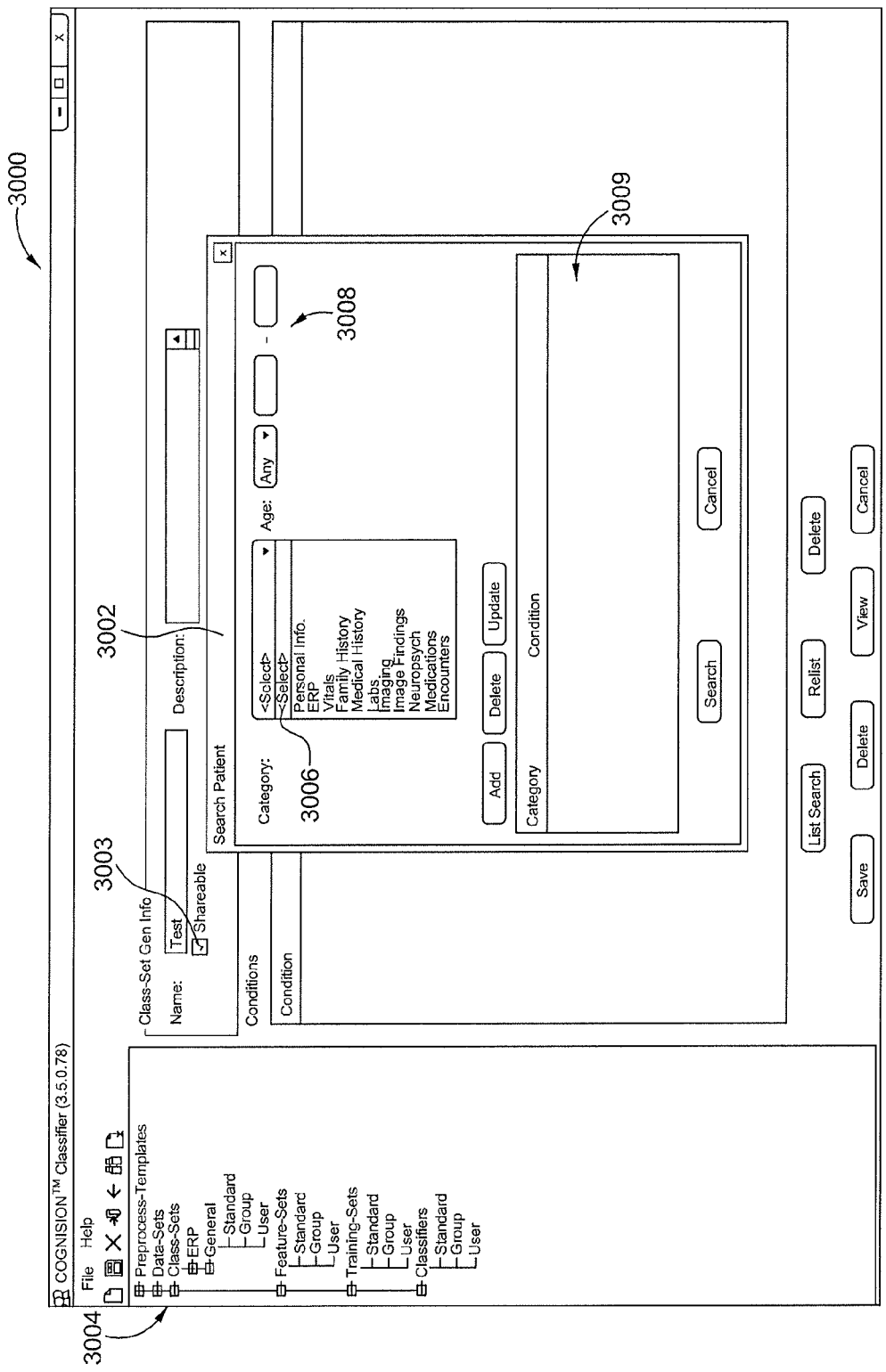
FIG. 13 depicts an exemplary screenshot view of an exemplary user interface for the biomarker fusion system of FIG. 11, showing a class set definition selection box.

FIGS. 13-18 show exemplary user interfaces providing selections for class sets. In particular, FIG. 13 shows an exemplary user interface (3000) comprising a search patient dialog box (3002). Search patient dialog box (3002) may be the first screen that the user encounters. It will be appreciated that user interface (3000) screens may be viewed/interacted with in the exemplary order presented. Alternatively, user interface (3000) screens may be used in any suitable order as would be apparent to one of ordinary skill in the art in view of the teachings herein. Additionally, a user may jump between or return to particular user interface (3000) screens as would be apparent to one of ordinary skill in the art in view of the teachings herein.

As seen in the present example, search patient dialog box (3002) may be used to create a class set definition using a drop down menu (3006) to select various biomarkers/parameters that will be used to define the class set. It will be appreciated that any suitable selection method may be used. Drop down menu (3006) lists the various biomarker information types contained in biomarker database (1002). For example, if biomarker information for a particular biomarker is not available, then drop down menu (3006) will not display such information despite being able to do so. Once the type of biomarker is selected through drop down menu (3006), a variable selection area (3008) is presented to the user for selection of a range of variable values within that biomarker type. Variable selection area (3008) is able to dynamically change the types of variables that can be selected, based on the biomarker type selected by the user. For example, if the selected age as a biomarker type, then the variable selection area will (3008) change its selection choices such that the only selectable choices describe potential age ranges. In the event that the selected biomarker type is a lab test, then variable selection area (3008) may comprise a series of test result possibilities.

As can also be seen in FIG. 13, a rights tree (3004) allows the user to define class set definitions once for users, groups, or as a standard/default group. A sharable box (3003) may be selected by a user which allows the class set definition to be shared with other users that may be part of the same group as the user. Furthermore, it will be appreciated that a class set definition, a feature set definition, etc. may be shared with any appropriate users, groups, and or standard/default group. It should also be understood that definitions set at one location may be shared with computers (511) at other locations.

Figure 14:
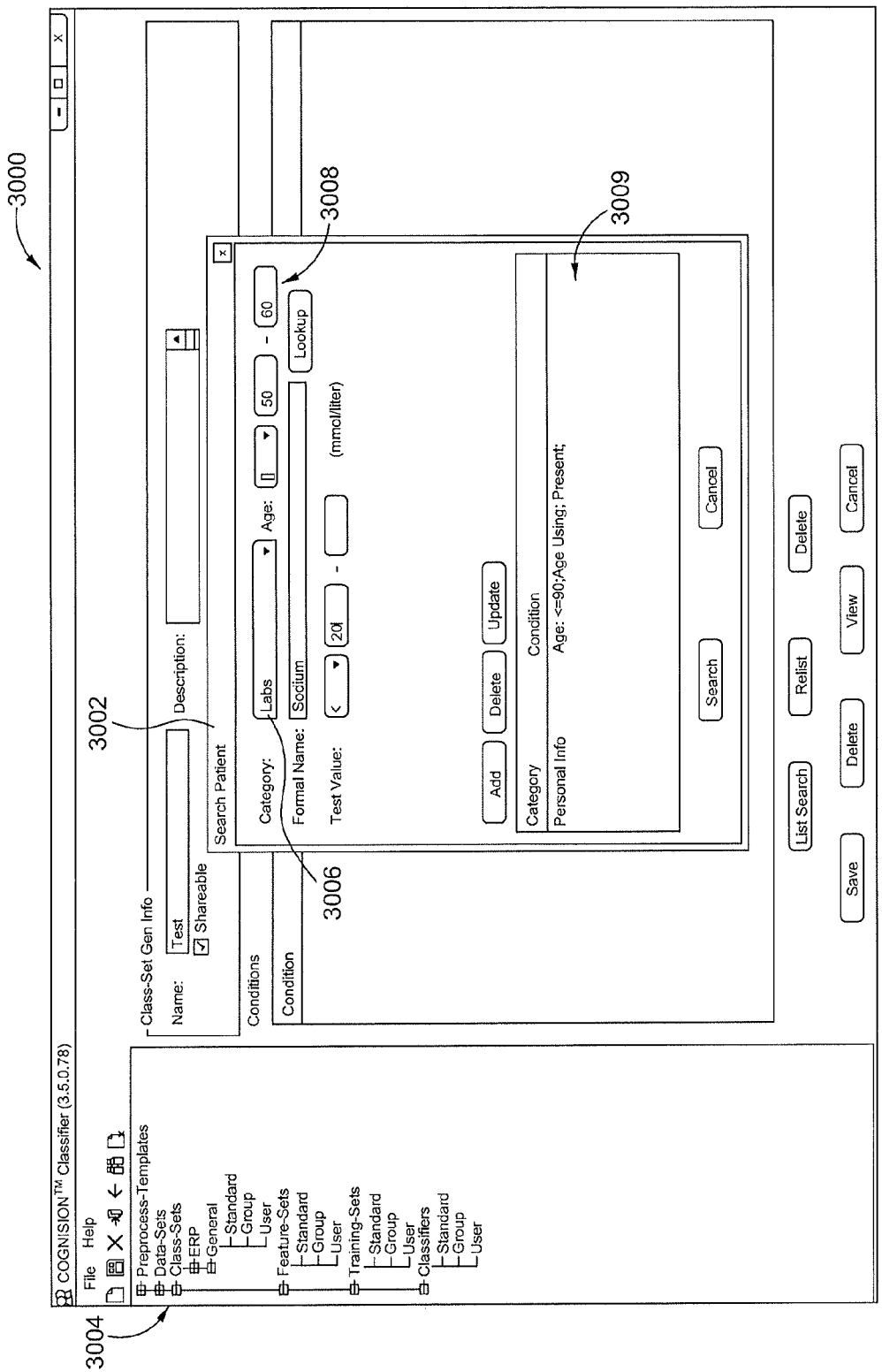
FIG. 14 depicts an exemplary screenshot view of an exemplary user interface for the biomarker fusion system of FIG. 11, showing a class set definition selection box after a first class set definition has been selected.
Figure 15:
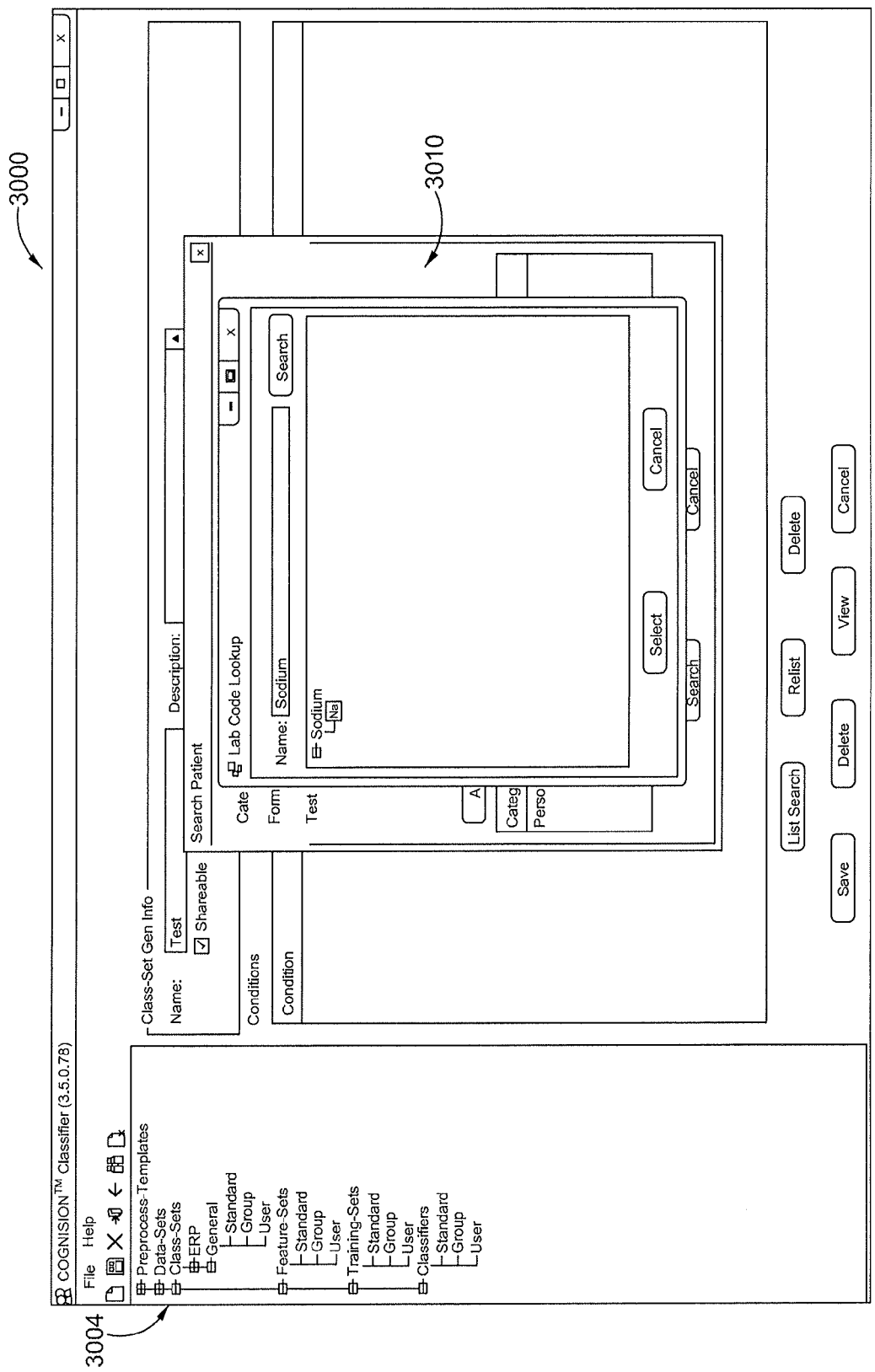
FIG. 15 depicts an exemplary screenshot view of an exemplary user interface for the biomarker fusion system of FIG. 11, showing a lab code lookup box.

Once a first biomarker/parameter is selected, FIG. 14 shows a second biomarker/parameter being selected to further define the class set. Thus, at the stage in FIG. 14, the user is selecting another biomarker to add to the class set definition. As can be seen in FIG. 14, a confirmation region (3009) shows that the user has already selected a biomarker parameter of patients/subjects who are presently less than or equal to 90 years of age. In the example shown in FIG. 14, the selected second biomarker parameter is a sodium lab test, but it will be appreciated that any other suitable second biomarker parameter may be used. FIG. 15 shows an exemplary lab code lookup box (3010) that is triggered by the user clicking on the "Lookup" button in FIG. 14. Lab code lookup box (3010) allows a user to select a lab test based on a standardized code for referring to the particular test result. Such functionality may be enabled by connecting to an online database and/or a standardized online database, such that software (510) is operable to pull lab test codes from a suitable external source in order to populate the list of available lab codes for lab code lookup box (3010). Furthermore, disease codes may also be extracted/imported from online databases. In some other versions, the lab test code data is stored locally, such that an online connection is not necessarily required.

Figure 16:
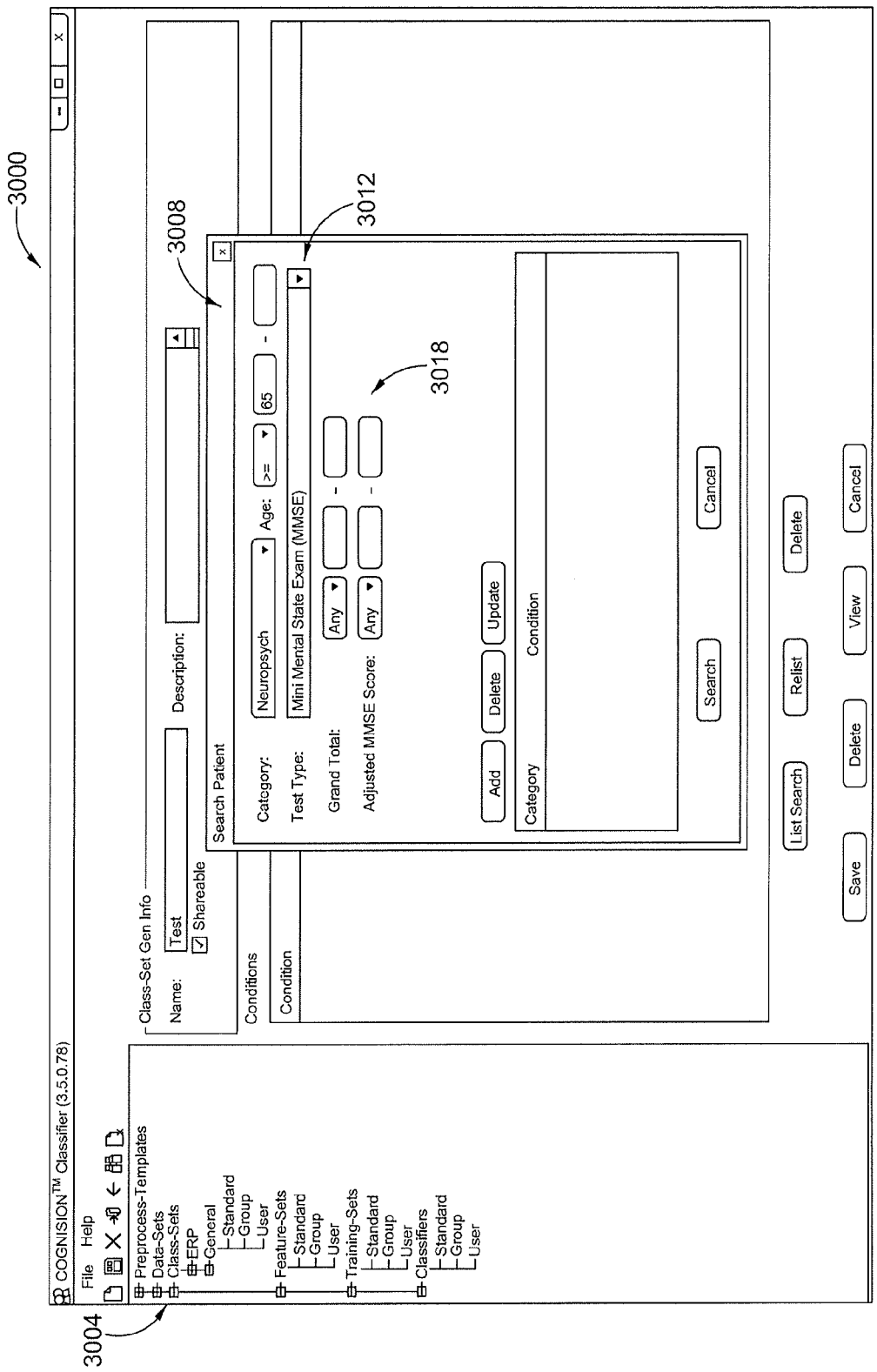
FIG. 16 depicts an exemplary screenshot view of an exemplary user interface for the biomarker fusion system of FIG. 11, showing a feature set definition selection box.

FIG. 16 shows an example of variable selection area (3008) where the user has selected neurosychology as the type of biomarker to be used in formulating a class set definition. This selection has triggered presentation of a neurosychology test type drop-down menu (3012). The user has selected mini mental state exam (MMSE) as the type of neurosychology test type, which has further triggered presentation of a scoring selection area (3018) that enables the user to select a grand total range for MMSE test scores and a range for adjusted MMSE scores. Incidentally, FIG. 16 also shows that the user has put a time restriction on this biomarker, selecting results for only patients/subjects who are at least 65 years of age.

Figure 17:
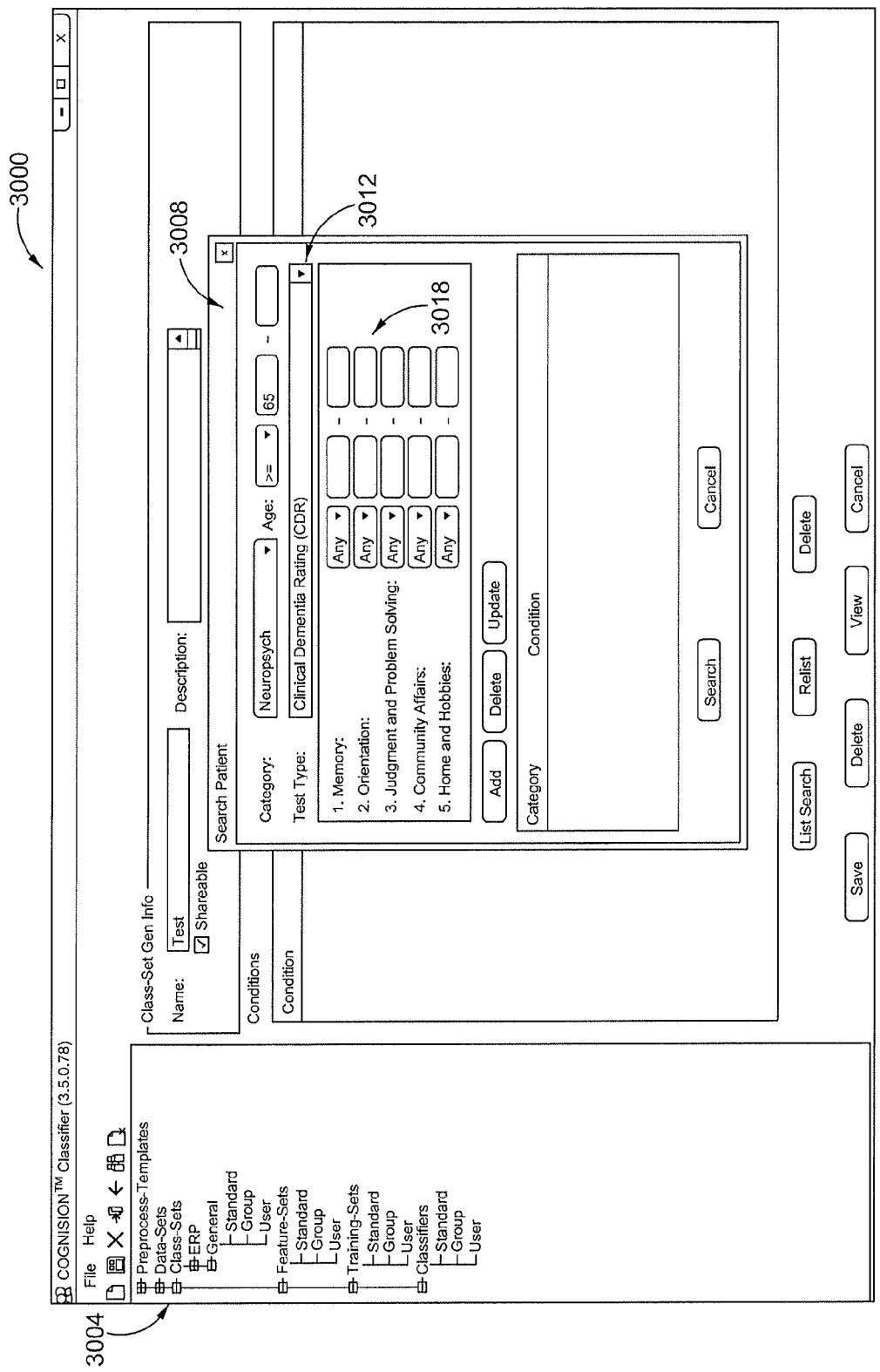
FIG. 17 depicts an exemplary screenshot view of an exemplary user interface for the biomarker fusion system of FIG. 11, showing a feature set definition selection box.

FIG. 17 shows another example of variable selection area (3008) where the user has selected neurosychology as the type of biomarker to be used in formulating a class set definition. However, in this example, the user has selected clinical dementia rating (CDR) from neurosychology test type drop-down menu (3012). This has triggered presentation of different types of variables in scoring selection area (3108), based on the selection of CDR rest type. Other various types of neurosychology tests (or other tests/biomarkers/etc.) that may be made available for selection will be apparent to those of ordinary skill in the art in view of the teachings herein. Similarly, the types of variables that may be presented to a user in scoring selection area (3018), based on selected test type and/or based on other factors, will be apparent to those of ordinary skill in the art in view of the teachings herein.

Figure 18:
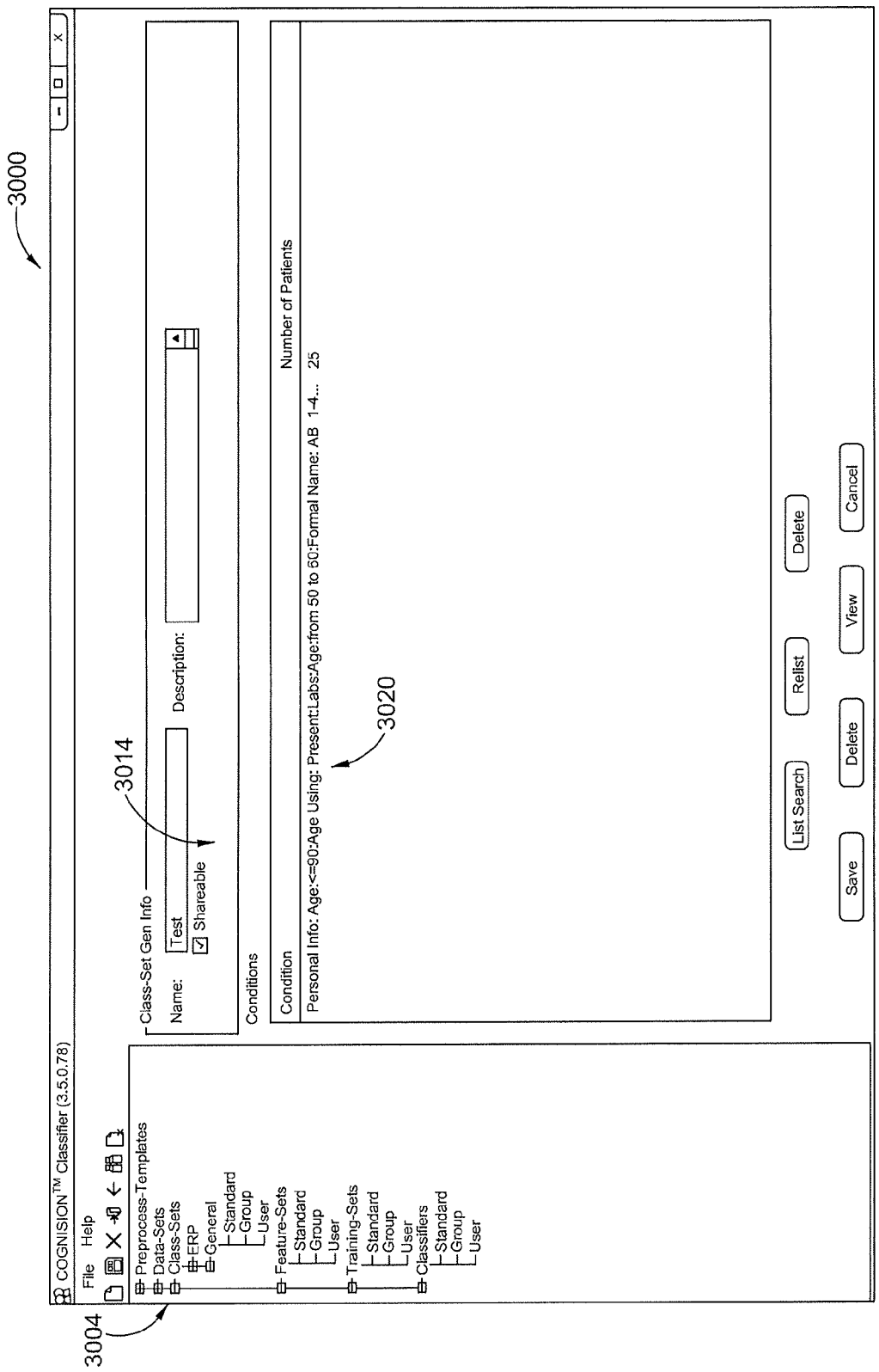
FIG. 18 depicts an exemplary screenshot view of an exemplary user interface for the biomarker fusion system of FIG. 11, showing a results screen.

FIG. 18 shows an exemplary results screen (3014) that may appear after a class set has been defined. In particular, results screen (3014) shows the total number of patients/subject in the database that match the class set definition. In the exemplary version, the total number of patient matches is 25, but it will be appreciated that other results may be generated based on the set definitions used as well as the biomarker pool and patient pool used. Results screen (3014) also includes a confirmation region (3020), showing the various parameters that were used to define the class set. In this example, those parameters include the patient's/subject's age being less than or equal to 90; and the patients/subjects having results of a certain type test within a certain range when the patient/subject was between the ages of 50 and 60.

Of course, the class sets relating to what is shown in FIGS. 13-18 mere examples. Various other formulations for class sets, including various combinations of biomarkers/parameters and values/ranges for variables associated with biomarkers, will be apparent to those of ordinary skill in the art in view of the teachings herein. It should also be understood that biomarker fusion system (15) may include a plurality of predefined class sets, in addition to or in lieu of enabling customized user-created definitions of class sets.

Figure 19:
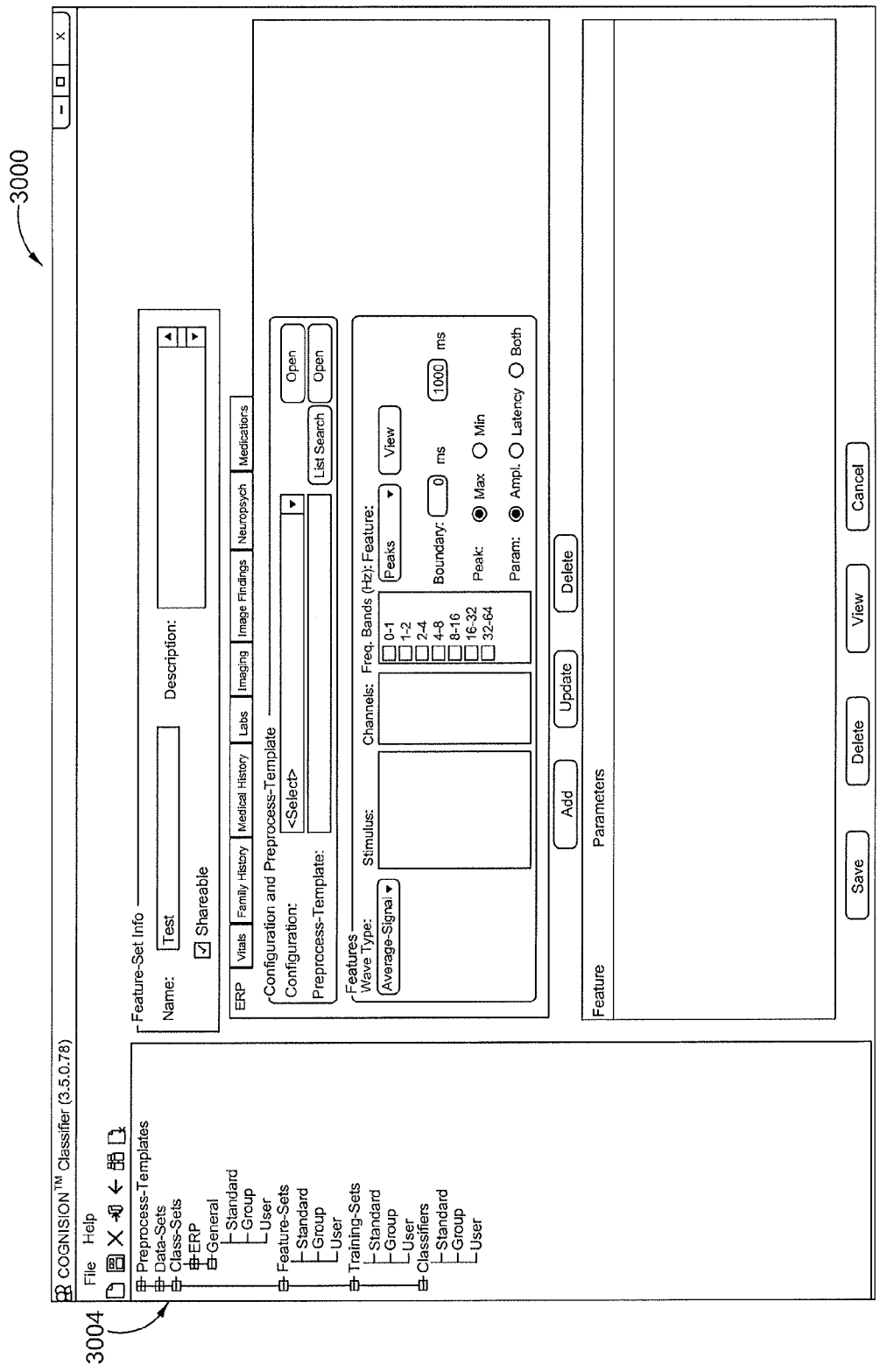
FIG. 19 depicts an exemplary screenshot view of an exemplary user interface for the biomarker fusion system of FIG. 11, showing a list of potential features.
Figure 20:
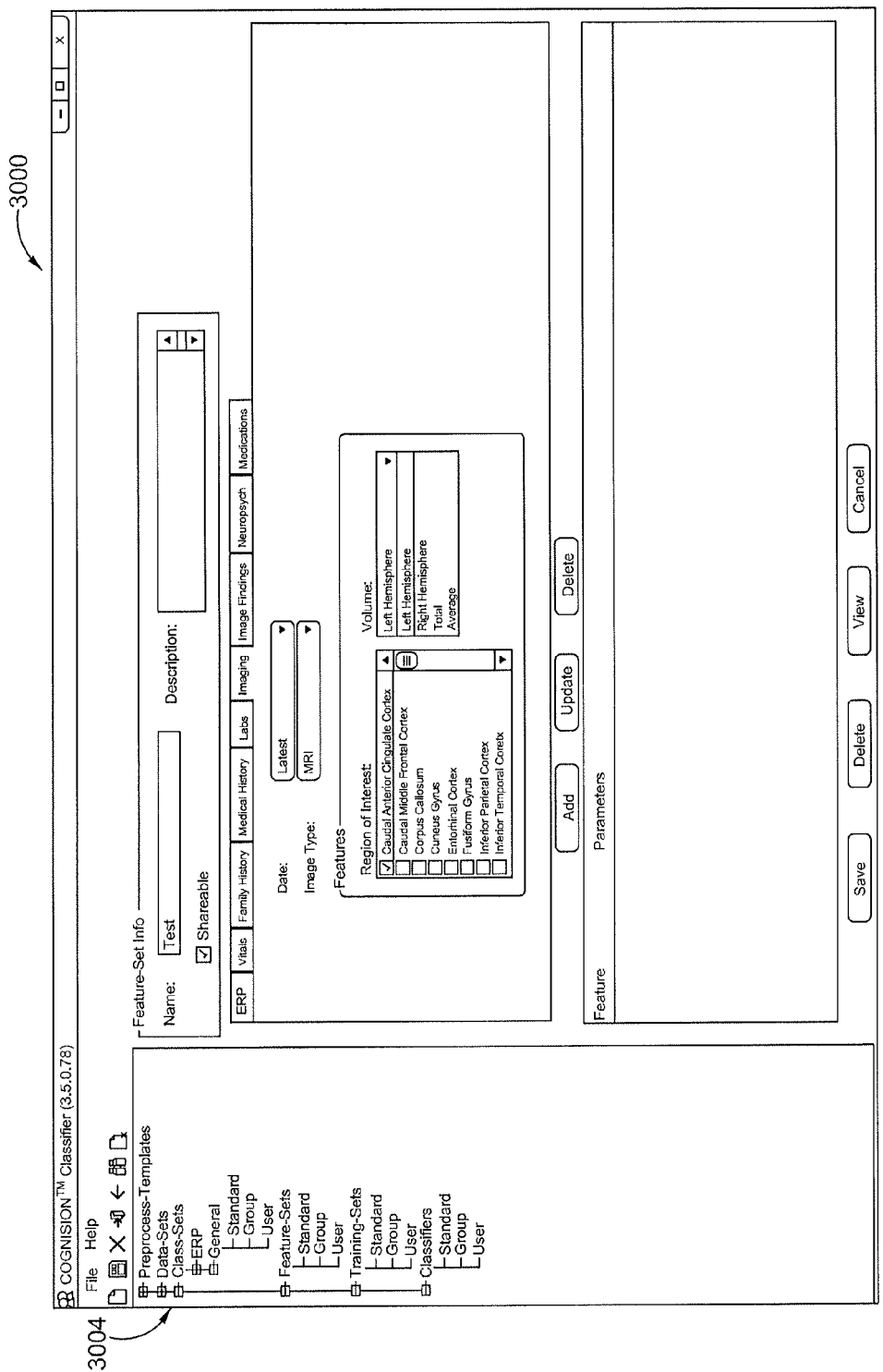
FIG. 20 depicts an exemplary screenshot view of an exemplary user interface for the biomarker fusion system of FIG. 11, showing an imaging feature set definition being selected.
Figure 21:
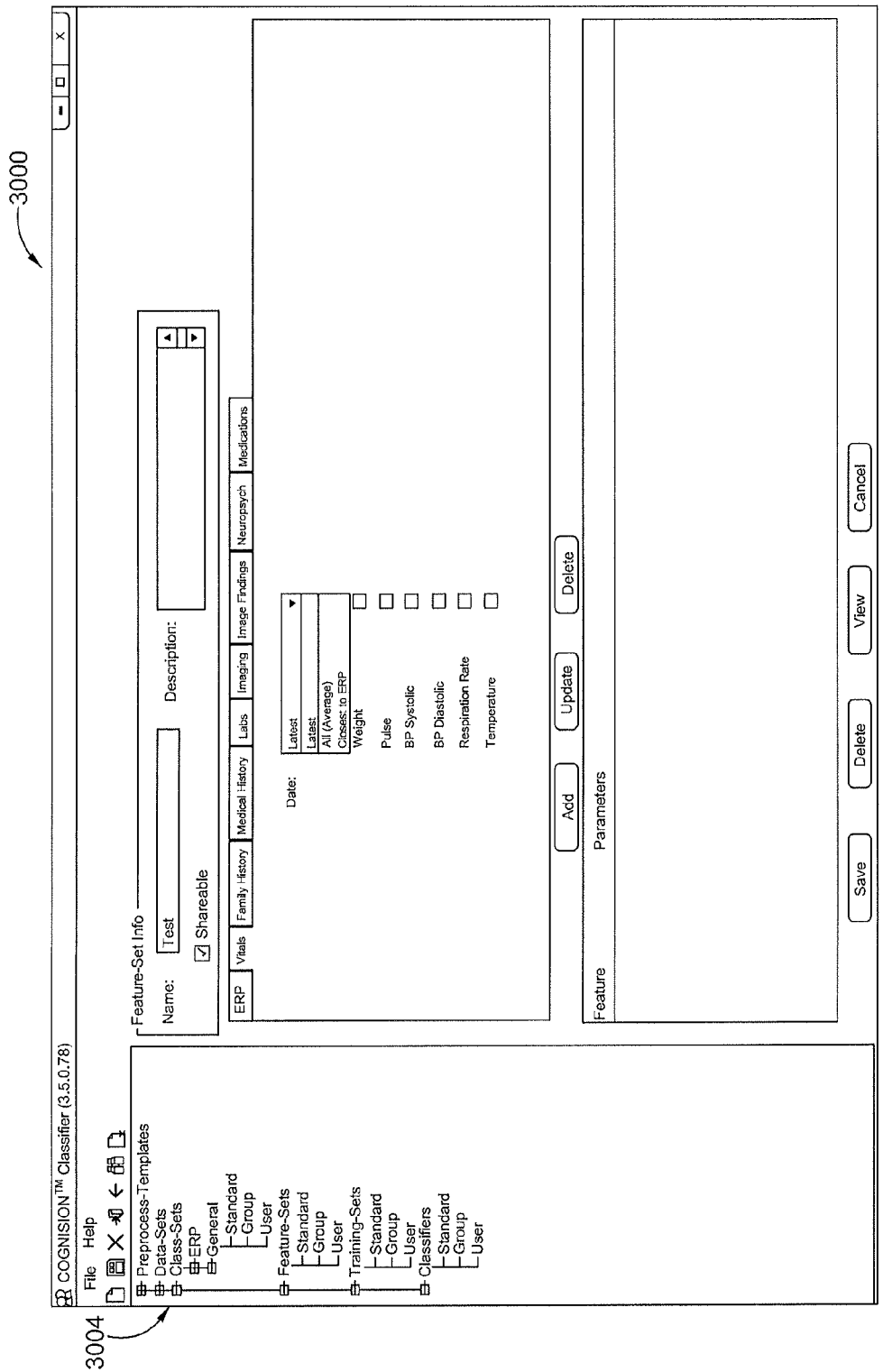
FIG. 21 depicts an exemplary screenshot view of an exemplary user interface for the biomarker fusion system of FIG. 11, showing the latest biomarker information being selected.

FIGS. 19-21 show user interfaces providing selections for feature sets. In the present example, feature sets are defined by biomarker parameters that are not the same as biomarker parameters that were used to define the class sets. Biomarker fusion system (512) may be configured to determine which class set a particular patient/subject belongs to based on feature set selections. Biomarker fusion system (512) thus uses feature sets to classify a patient/subject in one of two or more class sets. For instance, biomarker fusion system (512) may process data associated with patients/subjects that are inside and outside the defined class set to find correlations between that historical data and the data of the feature set selected by the user. In other words, the feature set selections may relate to data known about the particular patient/subject at hand. FIG. 19 shows that various kinds of information may be used as a potential feature for classifying subjects from a plurality of class sets. As mentioned above, it will be appreciated that biomarker information may be used to define feature sets regardless of whether biomarker information is in raw data form or if biomarker information has been processed using preprocessing template (1004) or third party data analysis (1006) as shown in FIG. 11. FIG. 19 in particular shows various ERP related data that may be used to define a feature set. FIG. 20 shows various kinds of an imaging data (e.g., volume of a particular region of a patient's brain in an MRI test) that may be used to define a feature set. FIG. 21 shows various kinds of patient vitals that may be used to define a feature set. It should be understood that biomarker fusion system (512) may rely on latest values for biomarker information in addition to averages of available values, and values closest to another test may be selected.

Figure 22:
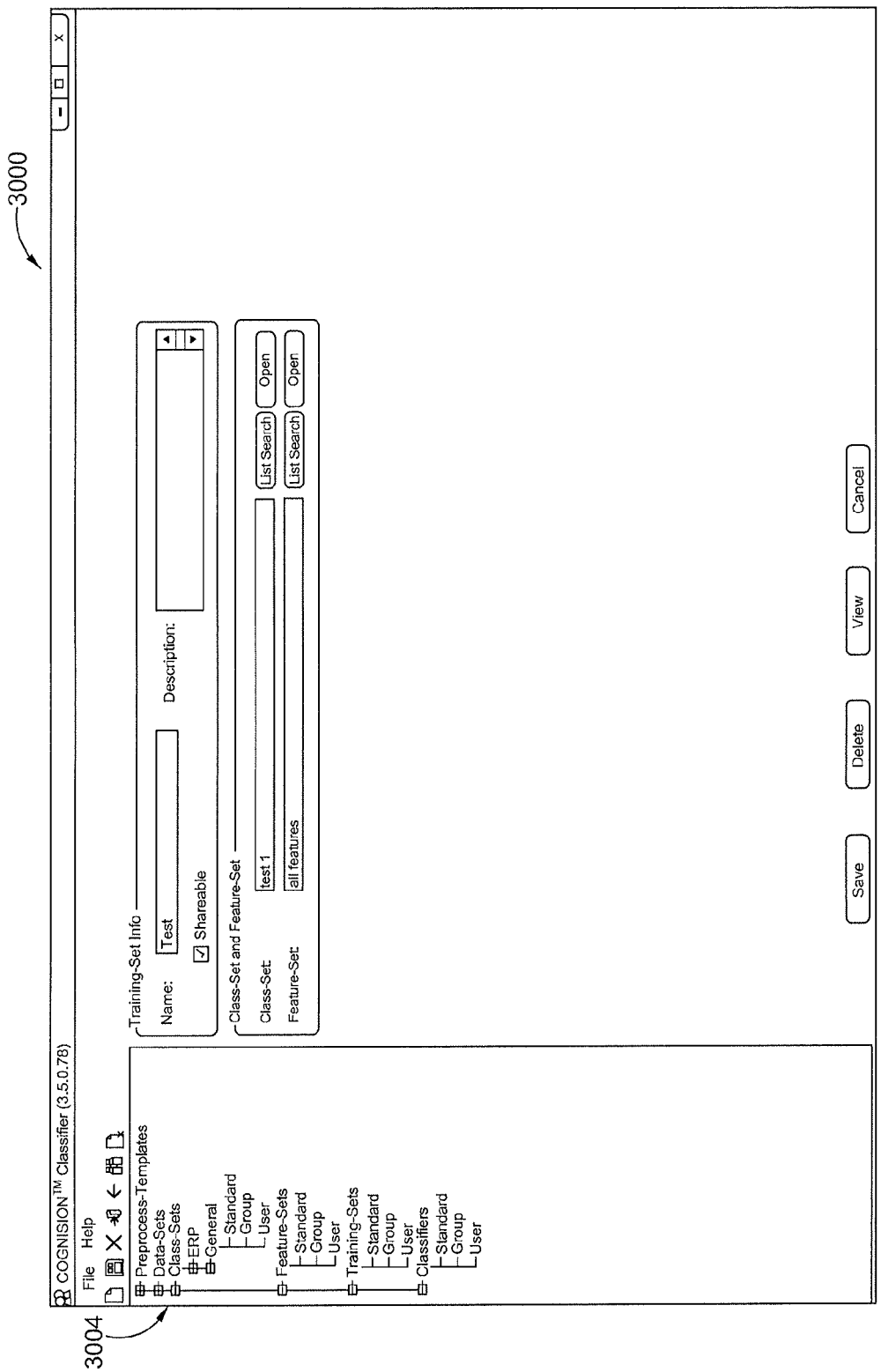
FIG. 22 depicts an exemplary screenshot view of an exemplary user interface for the biomarker fusion system of FIG. 11, showing the selection of a class set definition and a feature set definition.

FIG. 22 shows user interface (3000) allowing the user to define a training set by selecting a class set definition and a feature set definition. This process may include comparing the feature set definitions (e.g., the biomarker parameters and combinations thereof selected during the feature set definition process) against the data on hand for those patients/subjects who fit within the defined/selected class set. It will be appreciated that a validation test run may be used to verify that the same biomarker is not used for both feature set and class set.

Figure 23:
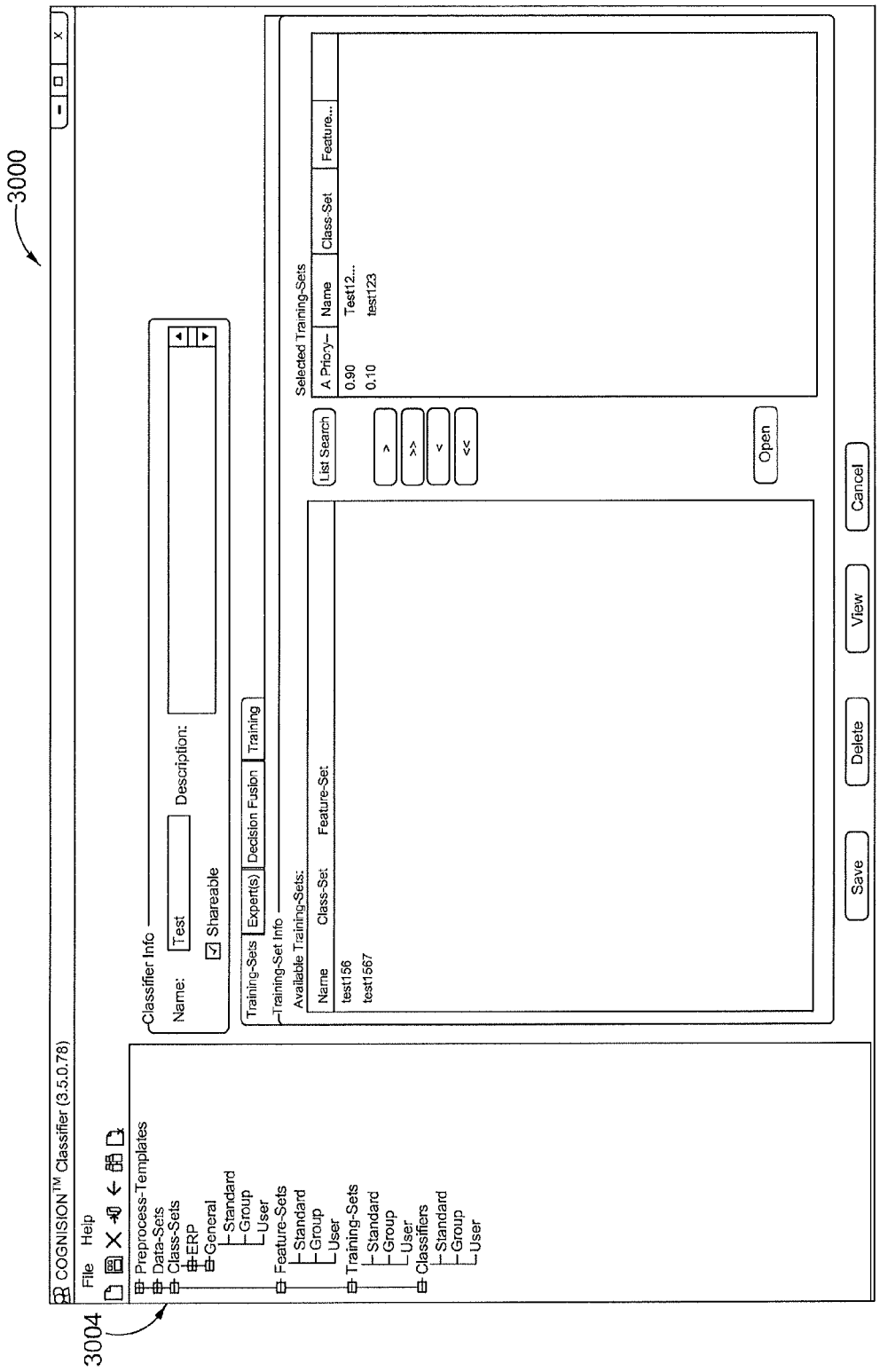
FIG. 23 depicts an exemplary screenshot view of an exemplary user interface for the biomarker fusion system of FIG. 11, showing the selection of training set definitions.

FIG. 23 shows user interface (3000) where training set definitions may be used to determine a classification schema, which may be used to ultimately process biomarkers from a patient and determine whether potential correlations with certain conditions may exist based on training set definitions, which may be used to render a diagnosis. In the exemplary version, two training set definitions are selected, but any suitable number of training sets may be selected. In addition, the user may set a-priori probabilities for the different training sets such that the classification schema is operable to calculate parameters related to the quality of the classifier such as Positive Predictive Value (PPV) and Negative Predictive Value (NPV).

Figure 24:
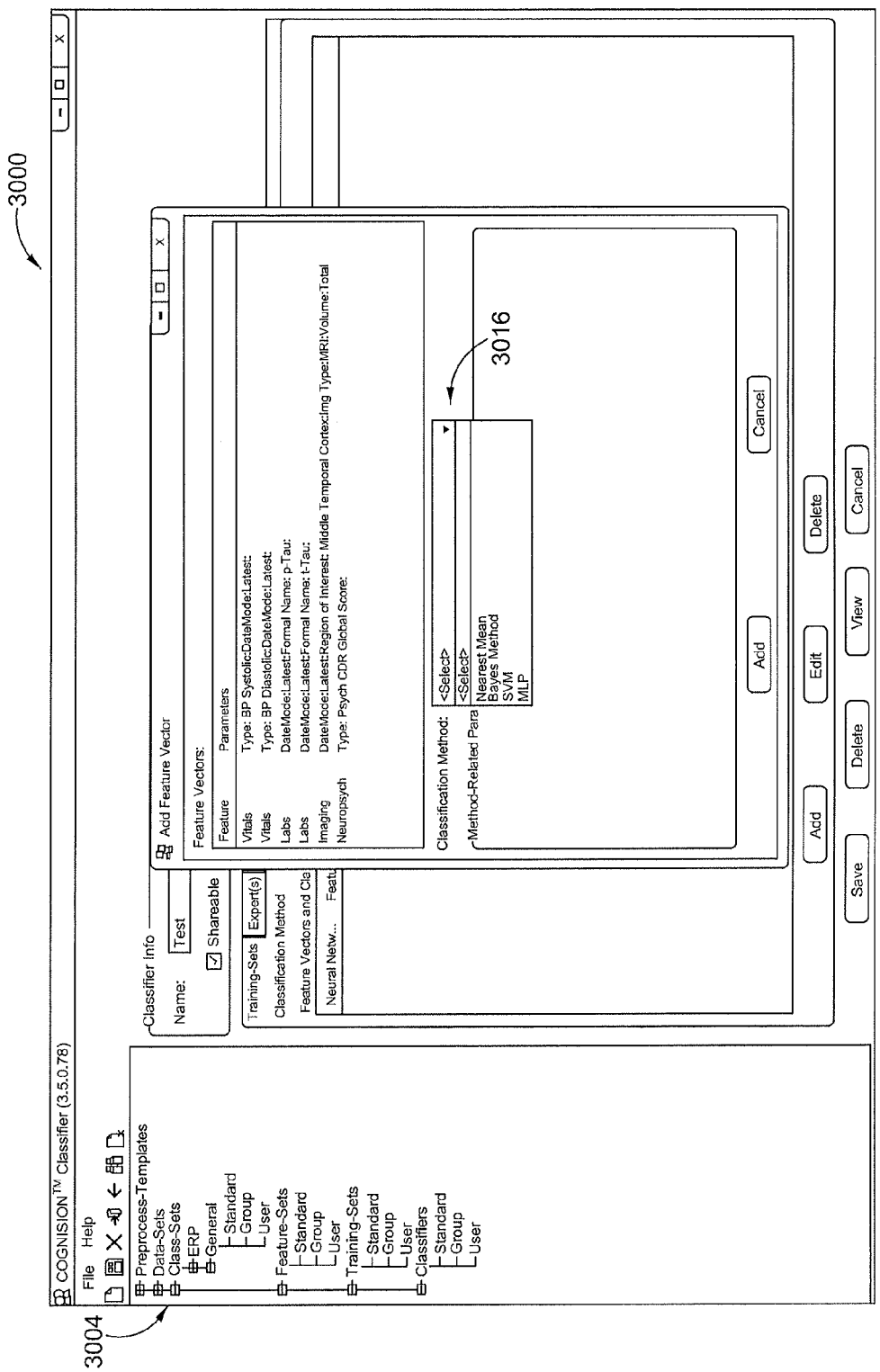
FIG. 24 depicts an exemplary screenshot view of an exemplary user interface for the biomarker fusion system of FIG. 11, showing the selection of individual experts.
Figure 25:
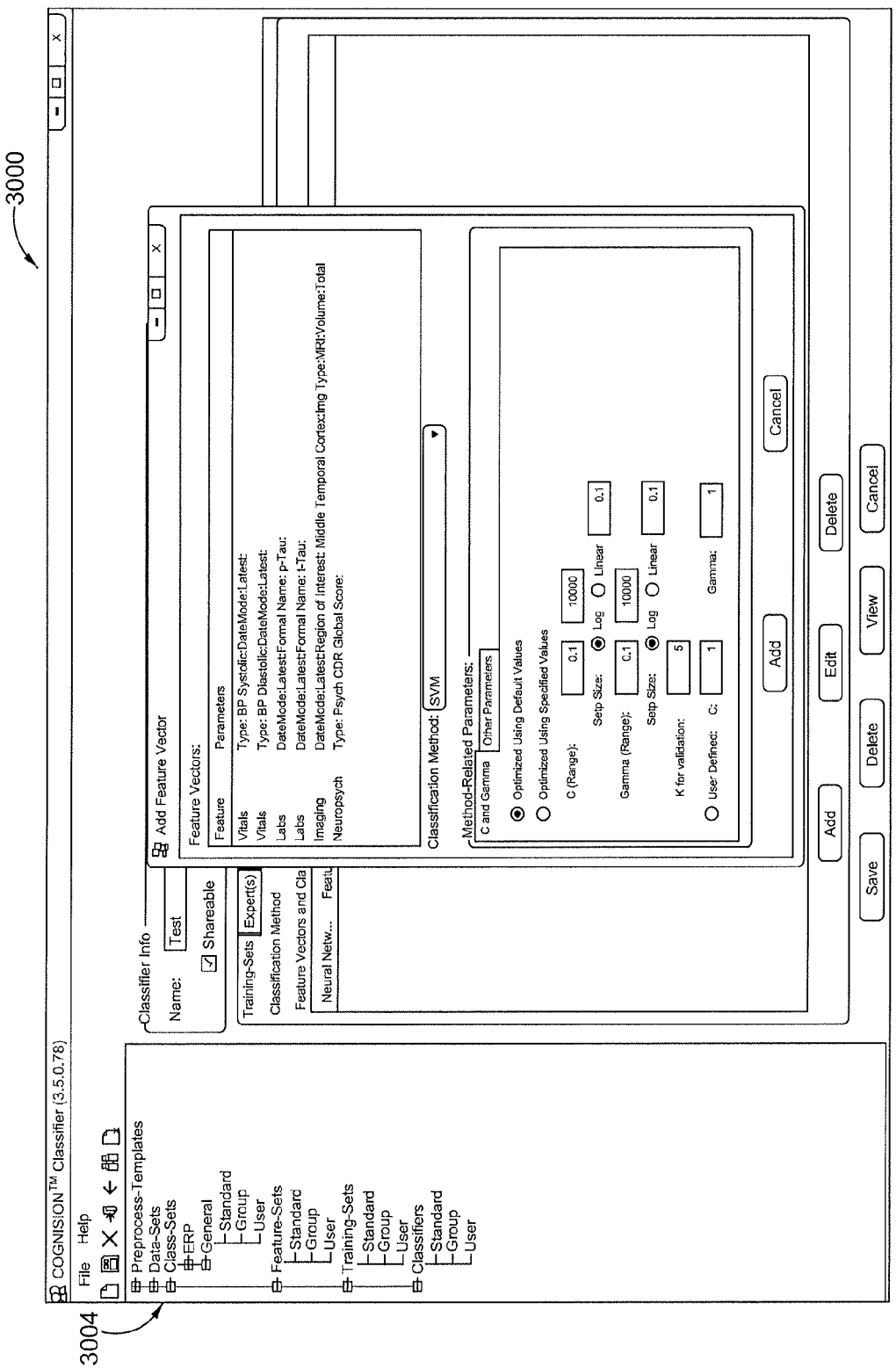
FIG. 25 depicts an exemplary screenshot view of an exemplary user interface for the biomarker fusion system of FIG. 11, showing the dynamically changing drop down menu after selecting an expert.
Figure 26:
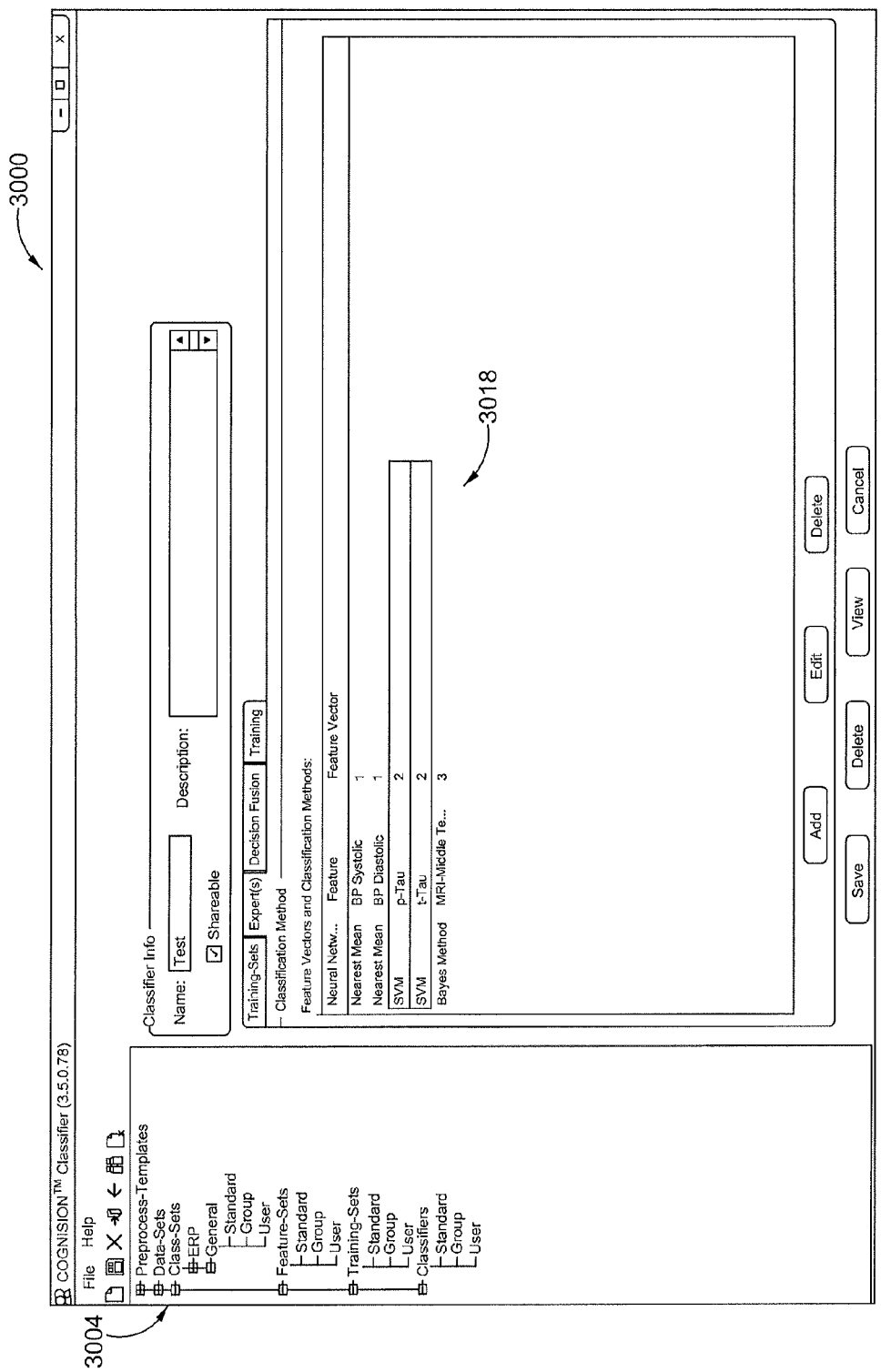
FIG. 26 depicts an exemplary screenshot view of an exemplary user interface for the biomarker fusion system of FIG. 11, showing a bank of experts.

FIG. 24 shows user interface (3000) where individual experts are defined, which may occur after training sets are defined as described above. User interface (3000) displays a list of available feature set vectors. It will be appreciated that in some versions, multiple features may be combined as inputs for a single machine learning algorithm as may be chosen from machine learning dropdown menu (3016). FIG. 25 shows how once a selection is made from dropdown menu (3016), user interface (3000) is operable to dynamically change based on the classification method selected. The user may thus further define how the selected algorithm will operate. FIG. 26 shows user interface (3000) displaying a bank of experts (3018) based on selections made through the user interface (3000) as shown in FIGS. 24-25, etc. This bank of experts (3018) may be used to perform processes through classifier module (1024) described above in the context of FIG. 11 and feature fusion stage (2002) described above in the context of FIG. 12.

Figure 27:
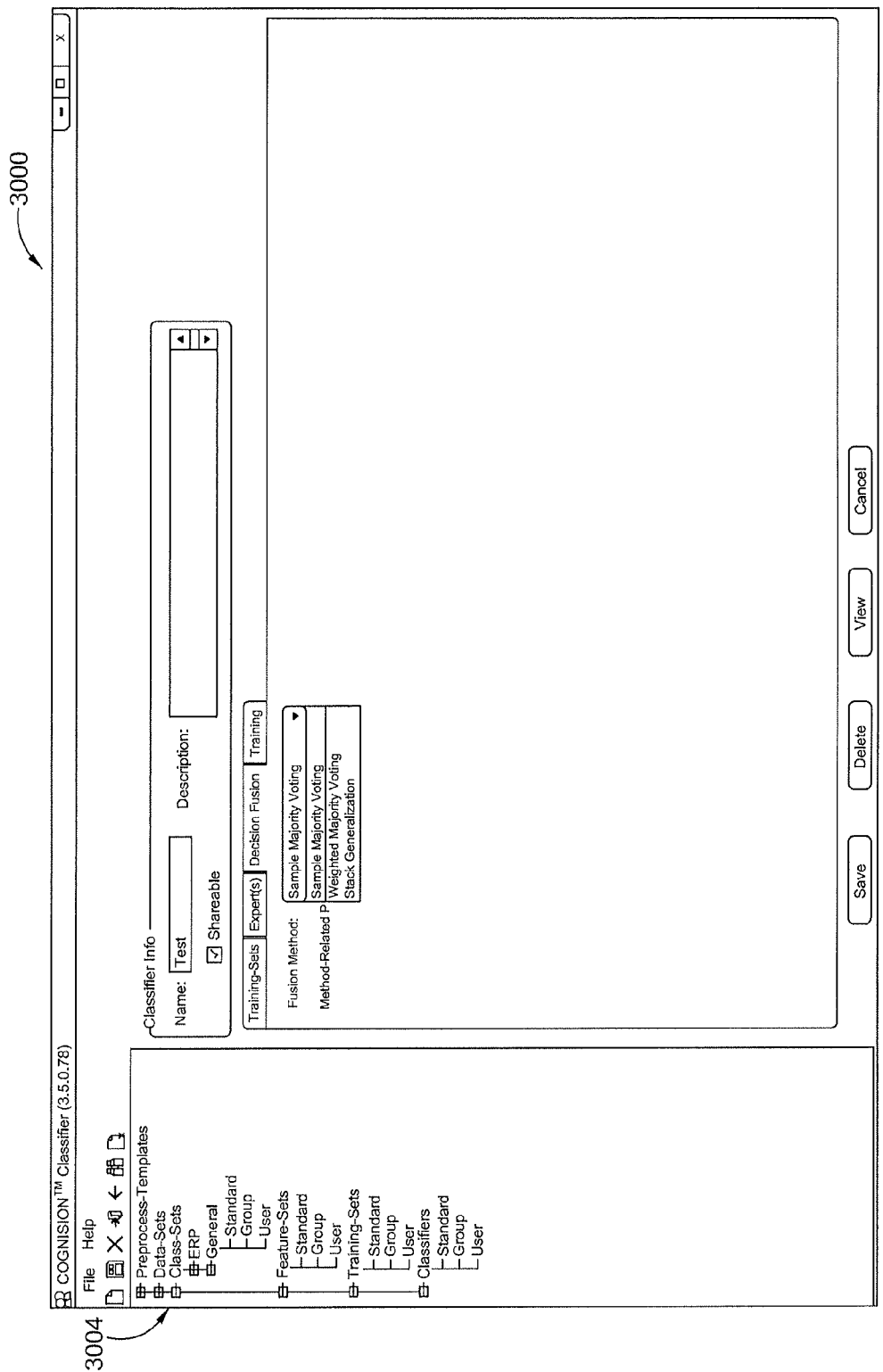
FIG. 27 depicts an exemplary screenshot view of an exemplary user interface for the biomarker fusion system of FIG. 11, showing the selection of various decision fusion algorithms.
Figure 28:
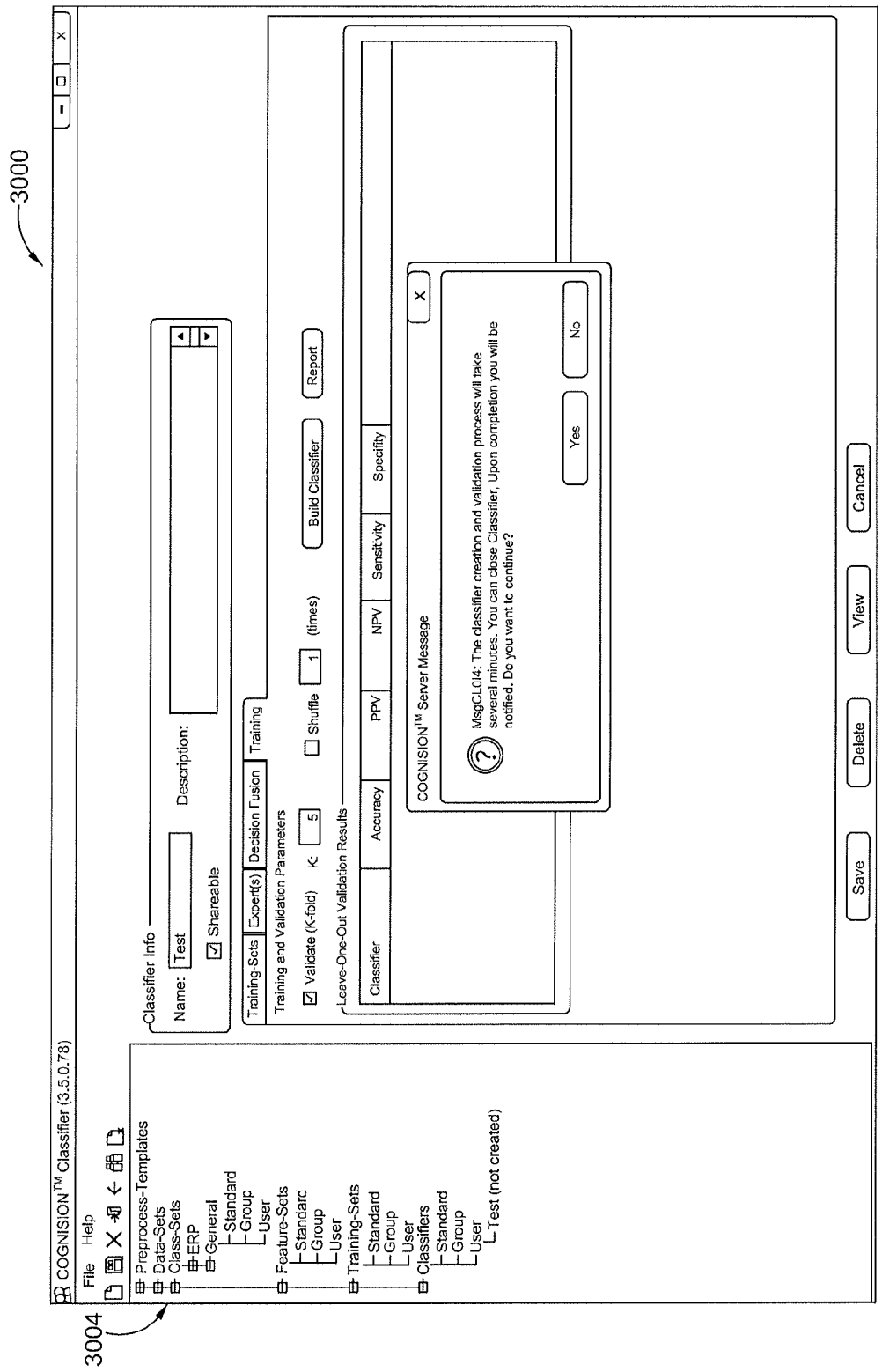
FIG. 28 depicts an exemplary screenshot view of an exemplary user interface for the biomarker fusion system of FIG. 11, showing a confirmation dialog box.

FIG. 27 shows user interface (3000) presenting user with various decision fusion algorithms operable to be selected by the user. It will be appreciated that based on the algorithm selected, different parameters may have to be selected. The various parameters to be set may be dynamically adjusted based on the algorithm selected. It should be understood that the decision fusion algorithm selected here may be used during the decision fusion stage (2004) described above in the context of FIG. 12. FIG. 28 shows a training screen of user interface (3000) that prompts the user to confirm that user wishes to continue after all of the necessary definitions and selections have been completed. After receiving confirmation from the user, biomarker fusion system (512) constructs a classifier based on the definitions and selections by the user. It will be appreciated that prior to this prompt, no data have been extracted or manipulated. Furthermore, the user may also select parameters that may allow for k-fold cross-validation and shuffle validation. Such validation processes may be performed in accordance with conventional k-fold and shuffle validation procedures.

Figure 29:
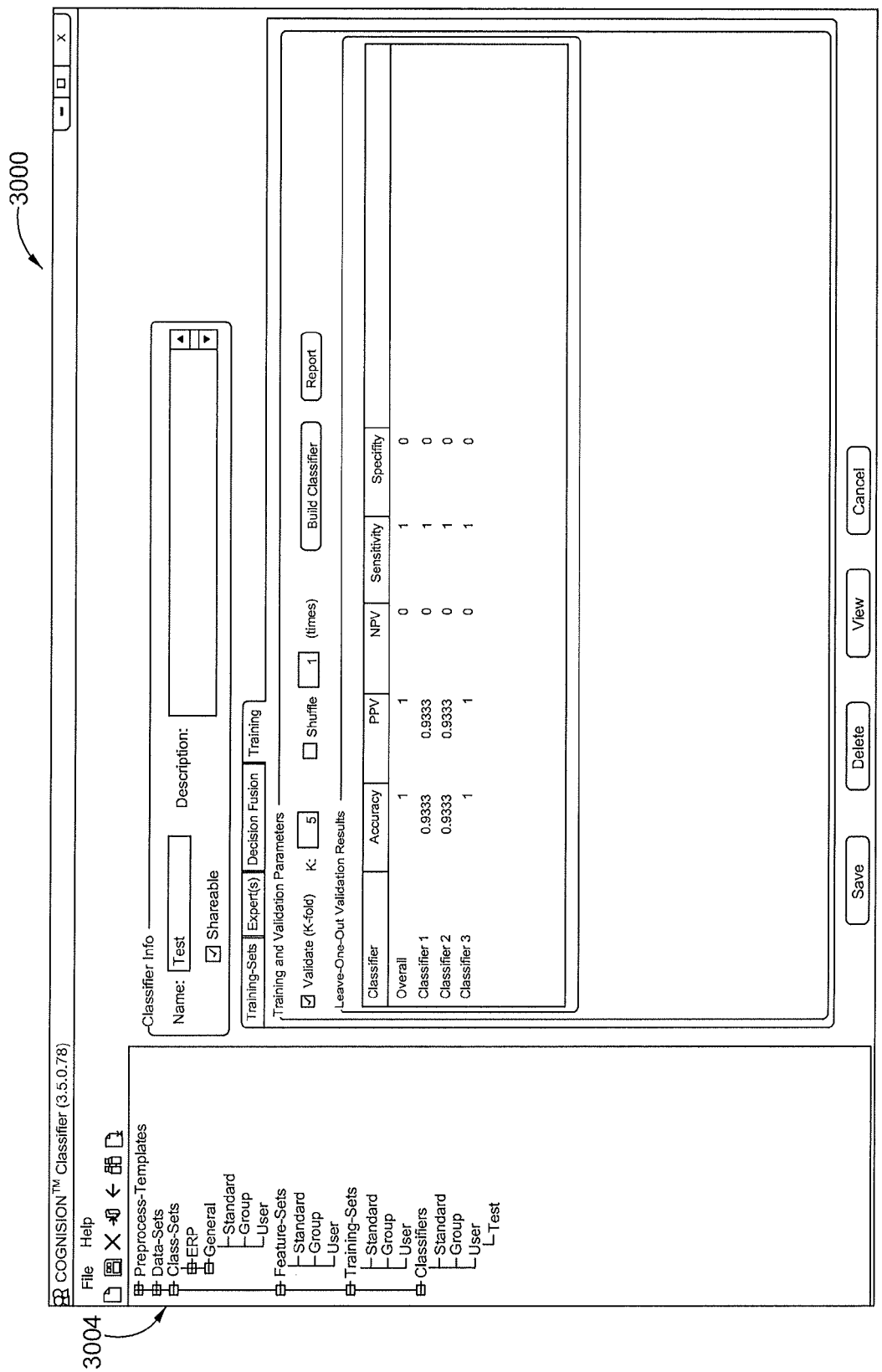
FIG. 29 depicts an exemplary screenshot view of an exemplary user interface for the biomarker fusion system of FIG. 11, showing the results of a classification.

FIG. 29 shows user interface (3000) providing the results of the classification build while providing reports on classification quality parameters that may have been selected in the process of forming the classifier. It should be understood that biomarker fusion system (512) has a modular architecture such that class sets, feature sets, and/or classification schema may be changed individually such that the user can easily assess the effects of the changes made to the classifier.

Figure 30:
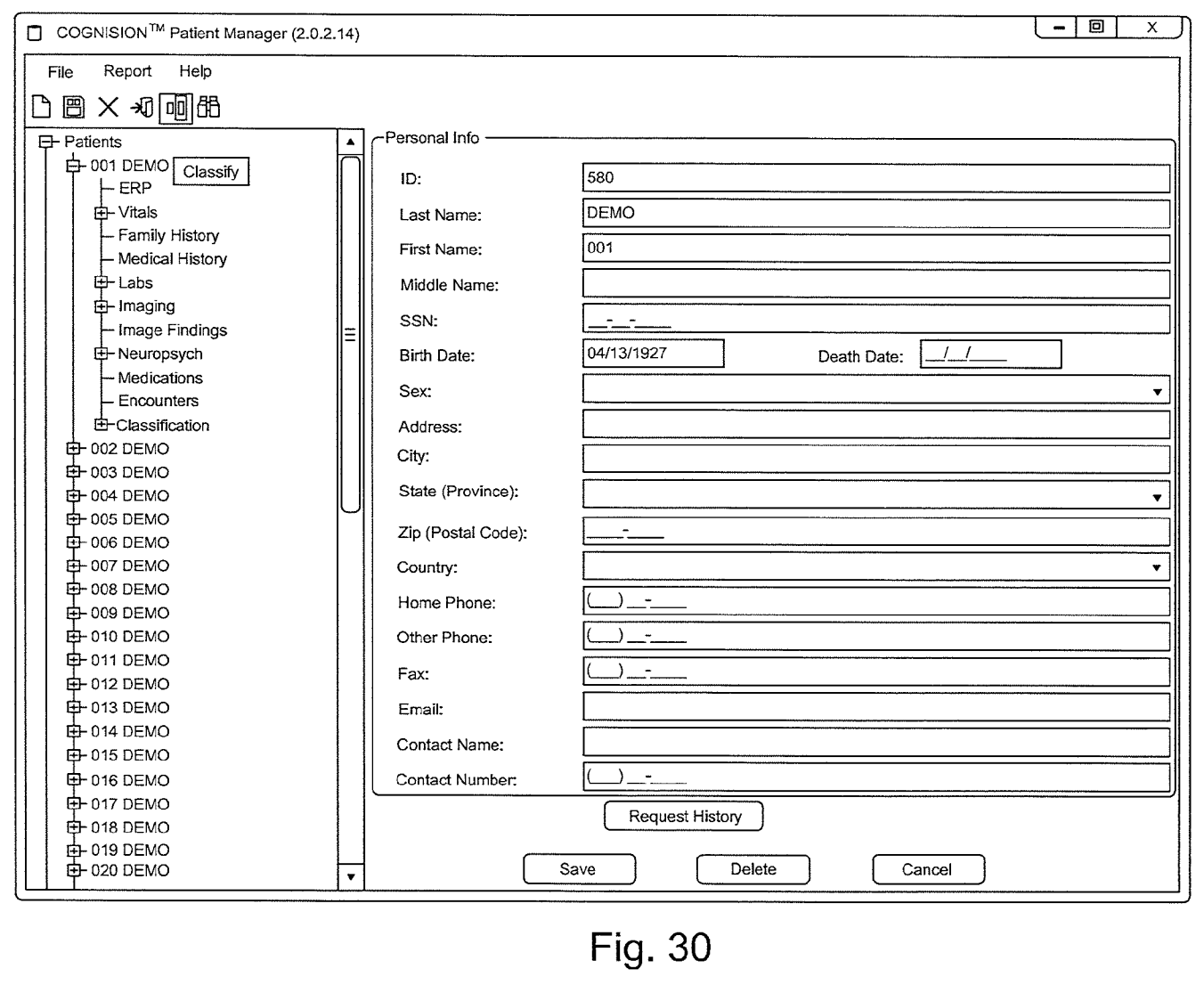
Figure 31:
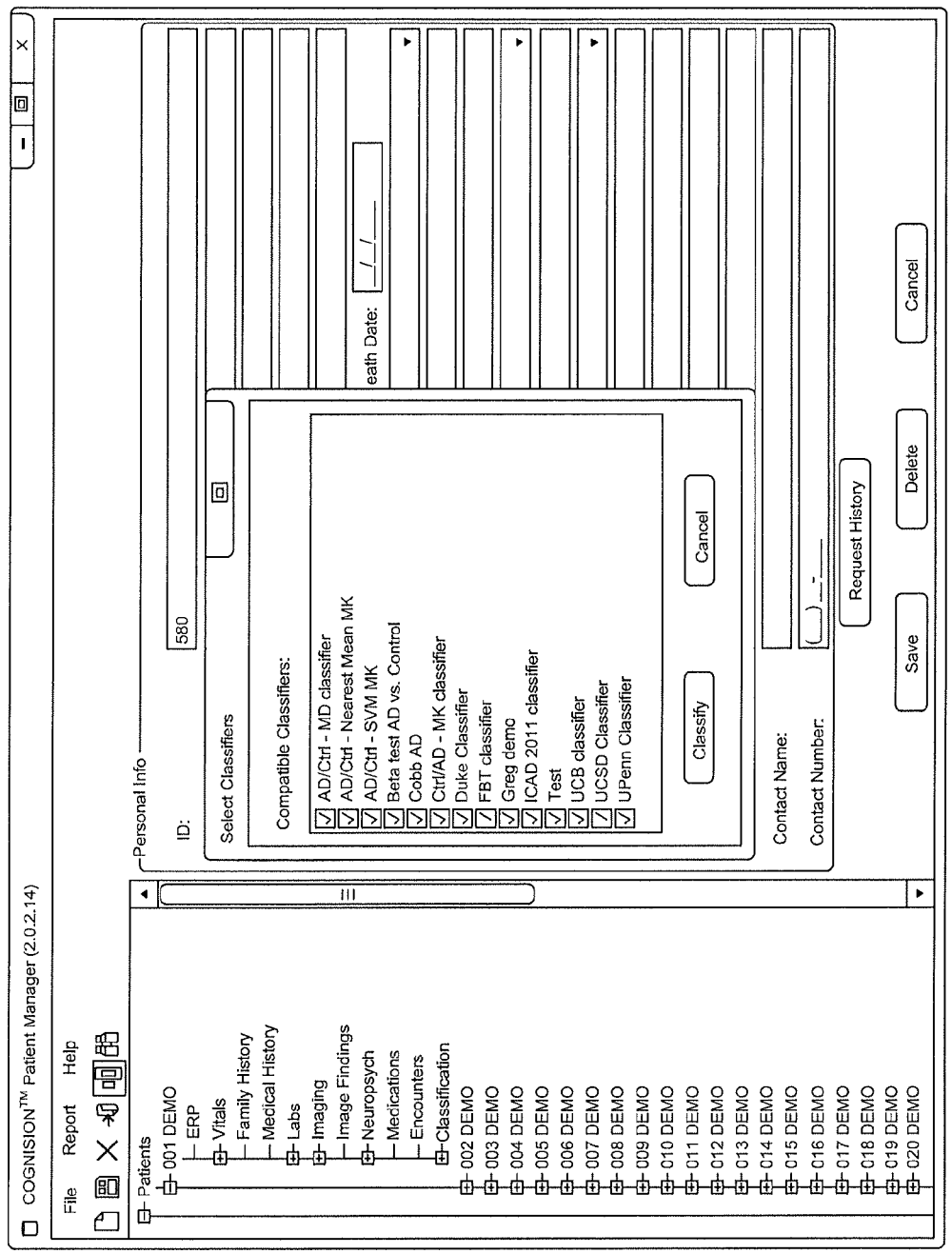
FIG. 31 depicts an exemplary screenshot view of an exemplary user interface for the biomarker fusion system of FIG. 11, showing a list of available classifiers for the one-touch classification window.
Figure 32:
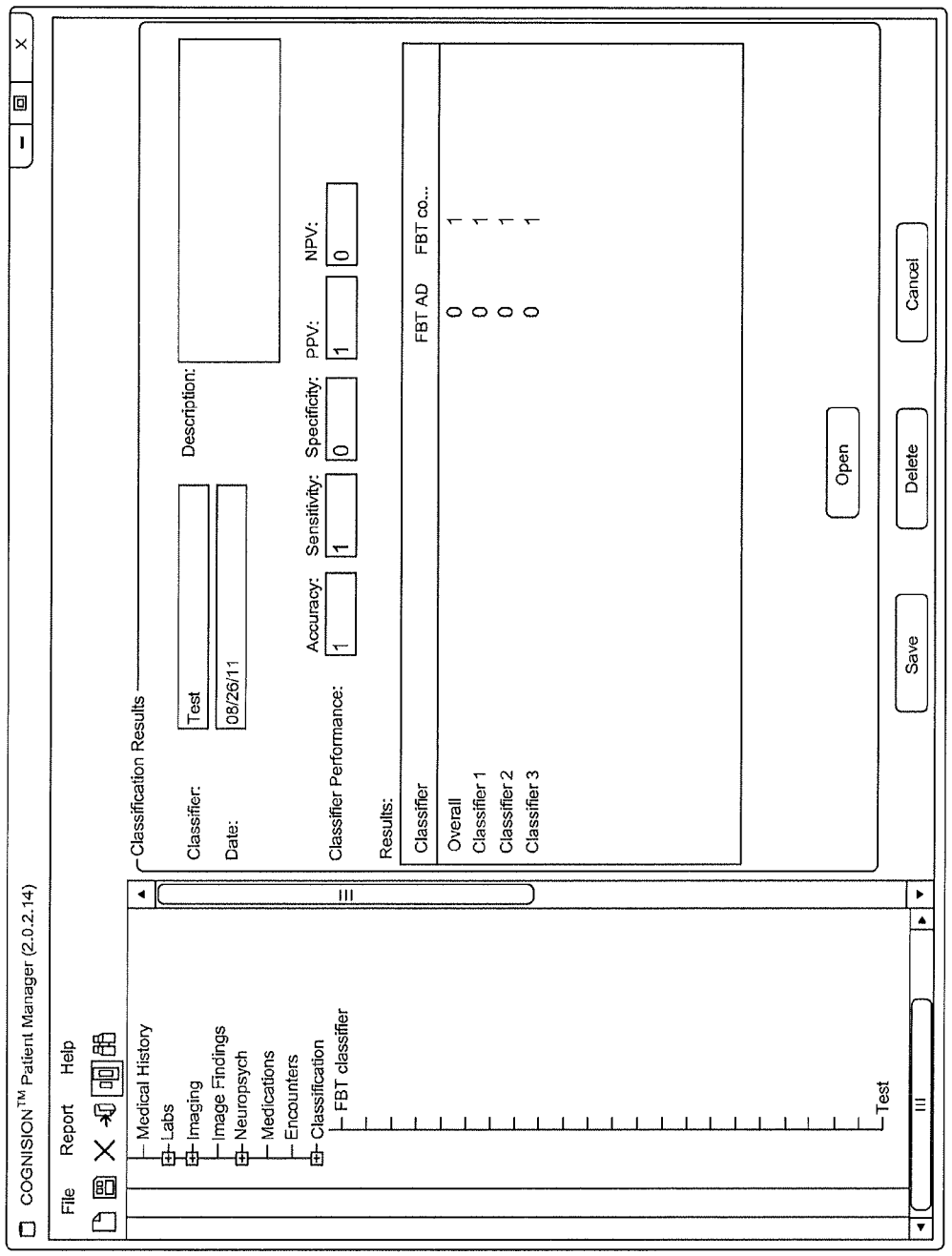
FIG. 32 depicts an exemplary screenshot view of an exemplary user interface for the biomarker fusion system of FIG. 11, showing a results screen for the one-touch classification window.

FIG. 30 shows an exemplary one-touch classification window (3018) where the user may simply press a button near a patient's name that is operable to initiate classification based on the patient's biomarker data. Furthermore, biomarker fusion system (512) is operable to analyze biomarker information for a patient to determine the list of available classifiers that may be used for the patient as seen in FIG. 31. Once a classification is performed on a patient, the result may be output as shown in FIG. 32. The user interface (3000) outputs classifier quality and the results of the classification. In the illustrated version, the results are shown in a tabulated format, but it will be appreciated that any suitable output format may be used as would be apparent to one of ordinary skill in the art in view of the teachings herein. Thereafter, the results may be stored as a classification record in the patient's data storage. Furthermore, the date of the classification tests may automatically be recorded.

It should also be understood that, in some versions, biomarker fusion system (512) may incorporate various teachings from U.S. Pub. No. 2008/0208072, entitled "Biopotential Waveform Data Fusion Analysis and Classification Method," published Aug. 28, 2008, the disclosure of which is incorporated by reference herein. Various suitable ways in which the teachings herein may be combined with the teachings of U.S. Pub. No. 2008/0208072 will be apparent to those of ordinary skill in the art.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of any claims that may be presented and is understood not to be limited to the details of structure and operation shown and described in the specification and drawings.

We claim:

1. An apparatus comprising:
(a) a ERP testing system, wherein the ERP testing system is configured to administer an ERP test;
(b) a computer in communication with the ERP testing system, wherein the computer is configured to access a database of biomarkers, wherein the computer is configured to select at least one class set definition and at least one feature set definition, wherein the at least one class set definition includes a class set based on a variable present in the database of biomarkers, wherein the feature set definition comprises a biomarker based on additional biomarker criteria, wherein the computer is configured to form at least one training set definition from the at least one class set definition and the at least one feature set definition;

wherein the computer is further configured to automatically render an original diagnosis by fusing biomarker data using the training set definition, wherein at least some of the fused biomarker data is acquired through the ERP testing system.

2. The apparatus of claim 1, wherein the computer is configured to make the training set definition available to multiple users.

3. The apparatus of claim 1, wherein the computer is configured to store the training set definition and export the training set definition.

4. The apparatus of claim 1, wherein the class set definition and the feature set definition each comprise a distinct biomarker.

5. The apparatus of claim 1, wherein the computer comprises a validation module operable to validate the at least one training set definition.

6. The apparatus of claim 1, wherein the computer is configured to connect to an online database to retrieve lab test codes for selecting the at least one class set definition.

7. The apparatus of claim 1, wherein the computer is configured to select a class set definition based on feature set information.

8. The apparatus of claim 1, wherein the computer is further configured to perform preprocessing to the database of biomarkers prior to selecting a feature set definition.

9. The apparatus of claim 1, wherein the computer is in communication with external software operable to perform image analysis to the database of biomarkers.

10. The apparatus of claim 1, wherein the computer is configured to display a dynamically updating selection box for selecting the at least one class set definition.

11. The apparatus of claim 1, wherein the computer is configured to display a dynamically updating selection box for selecting the at least one feature set definition.

12. The apparatus of claim 1, wherein the database of biomarkers comprises a SQL database.

13. The apparatus of claim 1, wherein the computer is configured to use a plurality of training set definitions to form a meta-model.

14. The apparatus of claim 1, wherein the computer further comprises an expert classifier module.

15. A system for constructing a meta-model, the system comprising:

(a) a computer configured to output a selection dialog for defining a class set, wherein the computer is further configured to output a second selection dialog for defining a feature set, wherein the computer is configured to combine the class set definition and the feature set definition into a training set definition, wherein the class set definition comprises a class set based on a first selected biomarker, wherein the feature set definition comprises a feature set based on a second biomarker, wherein the first biomarker and the second biomarker have no known relationship, wherein the training set definition is transmitted to an expert classifier module; and (b) a storage device configured to store a database of biomarker information, wherein the computer and the storage device are in communication with each other, wherein the computer is operable to retrieve biomarker information from the storage device in association with the expert classifier module;

wherein the computer is further configured to execute the expert classifier module to thereby automatically generate an original diagnosis of a patient exhibiting a biomarker used in at least one of the class set definition or the feature set definition.

16. The system of claim 15, wherein the storage device is configured to encrypt a portion of the biomarker information.

17. The system of claim 15, wherein the computer is configured to access the storage device to construct a list of possible class set definitions.

18. The system of claim 15, wherein the computer comprises a validation module operable to validate the training set definition.

19. The system of claim 15, wherein the storage device is configured to perform preprocessing to the biomarker information contained on the storage device.

* * * * *